(12) United States Patent
Roy et al.

(10) Patent No.: US 8,399,025 B2
(45) Date of Patent: Mar. 19, 2013

(54) POLYAMINE MODIFIED PARTICLES

(75) Inventors: Krishnendu Roy, Austin, TX (US); Sudhir Pai Kasturi, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 2091 days.

(21) Appl. No.: 11/145,589

(22) Filed: Jun. 6, 2005

(65) Prior Publication Data

US 2009/0110719 A1 Apr. 30, 2009

Related U.S. Application Data

(60) Provisional application No. 60/577,421, filed on Jun. 4, 2004.

(51) Int. Cl.
*A61K 51/00* (2006.01)

(52) U.S. Cl. .......................... 424/501; 424/489

(58) Field of Classification Search .................. 424/501, 424/489, 499; 514/951
See application file for complete search history.

(56) References Cited

U.S. PATENT DOCUMENTS

| 5,908,829 | A | * | 6/1999 | Kelly | 514/12 |
| 6,413,941 | B1 | | 7/2002 | Garnett et al. | 514/44 |
| 2004/0147466 | A1 | | 7/2004 | Barman et al. | 514/44 |
| 2005/0153913 | A1 | * | 7/2005 | Kosak | 514/44 |
| 2008/0102114 | A1 | * | 5/2008 | Koritala et al. | 424/456 |

FOREIGN PATENT DOCUMENTS

WO 90/09780 9/1990

OTHER PUBLICATIONS

Bivas-Benita et al., PLGA-PEI nanoparticles for gene delivery to pulmonary epithelium, 2004, European Journal of Pharmaceuticals and Biopharmaceutics, 58, pp. 1-6.*
S.P. Kasturi et al.; "Covelant conjugation of polyethyleneimine on biodegradable microparticles for delivery of plasmid DNA vaccines"; Biomaterials, vol. 26, pp. 6375-6385, 2005.
S.P. Kasturi et al.; PEI-Chitosan Grat Copolymers for Mucosal Delivery of Genetic vaccines (Abstract), 2004.
S.P. Kasturi; 2004 American Society of Gene Therapy poster presentation (PowerPoint Slides); pp. 12, 2004.
S. Dumitriu et al.; "Polysaccharaides in Medical Applications"; pp. 631-649, 1996.
Journal of Polymer Science: Part A: Polymer Chemisrty; "Structural Changes of pH-Sensitive Chitosan/Polymer Hydrogels in Different pH Solution"; vol. 32, pp. 591-596, 1994.
E. Tomlinson et al.; "Controllable gene therapy Pharmaceutics of non-viral gene delivery systems"; Journal of Controlled Release, vol. 39, pp. 357-372, 1996.
H. Terayama; "Method of Colloid Titration (A New Titration between Polymer Ions)"; Journal of Polymer Science, vol. 8, No. 2, pp. 243-253, 1952.
Artursson et al.; "Effect of Chitosan on the Permeability of Monolayers of Intestinal Epithelial Cells (Caco-2)"; Pharmaceutical Research, vol. 2, No. 9, pp. 4, 1994.
L. Illum et al.; "Chitosan as a Novel Nasal Delivery System for Peptide Drugs"; Pharmaceutical Research, vol. 11, No. 8, pp. 4, 1994.

K. Roy et al.; "Gene Delivery with In-situ Crosslinking Polymer Networks Generates Long-term Systemic Protein Expression"; Molecular Therapy, vol. 7, No. 3, pp. 401-408, 2003.
H. Gu et al.; "Topical permeation enhancers efficiently deliver polymer micro and nanoparticles to epidermal Langerhans' cells"; J. Drug Del. Sci. Tech., vol. 14, No. 4, pp. 265-273, 2004.
R. J. Mumper et al.; "Polyvinyl Derivatives as Novel Interactive Polymers for Controlled Gene Delivery to Muscle"; Pharmaceuticals Research, vol. 13, No. 5, pp. 701-709, 1996.
Z. Cui et al.; "Chitosan-based nanoparticles for topical genetic immunization"; Journal of Controlled Release, vol. 75, pp. 409-419, 2001.
C. E. Kast et al.; "Chitosan-thioglycolic acid conjugate: a new scaffold material for tissue engineering"; International Journal of Pharmaceutics, vol. 256, pp. 183-189, 2003.
A. Bernkop-Schnürch et al.; "Thiolated chitosans"; European journal of Pharmaceutical and Biopharmaceutics, vol. 57, pp. 9-17, 2004.
MX Tang et al.; "The influence of polymer structure on the interactions of cationic polymers with DNA and morphology of the resulting complexes"; Gene Therapy, vol. 4, pp. 823-832, 1997.
KS Denise-Mize et al.; "Plasmid DNA absorbed onto cationic microparticles mediates target gene expression and antigen presentation by dendritic cells"; Gene Therapy, vol. 7, pp. 2105-2112, 2000.
U. McKeever et al.; "Protective immune response elicited in mice by immunization with formulations of poly(lactide-co-glycolide) microparticles"; Vaccine, vol. 20, pp. 1524-1531, 2002.
K. Roy et al.; "Intramuscular delivery of DNA vaccines from sustained release microparticle formulations"; In: Fifth Cold Spring Harbor Conference on Gene Therapy, Sep. 25-29, 2000; New York: Cold Spring Harbor Laboratory (Abstract); p. 1, 2000.
M. Singh et al.; "Cationic microparticles: A potent delivery system for DNA vaccines"; Proc. Natl. Acad. Sci. USA, vol. 97, No. 2, pp. 811-816, 2000.
M.B. Lutz et al.; "An advanced culture method for generating large quantities of highly pure dendritic cells from mouse bone marrow"; journal of Immunological Methods, vol. 223, pp. 77-92, 1999.

(Continued)

*Primary Examiner* — James Rogers
(74) *Attorney, Agent, or Firm* — Baker Botts L.L.P.

(57) ABSTRACT

A particle composition comprising a graft copolymer formed from a biocompatible polymer and a plurality of polyamine moieties, wherein the polyamine moieties are bound to the biocompatible polymer, and a combinatorial delivery polymer comprising a plurality of particles that comprises a graft copolymer of formed from a biocompatible polymer and a plurality of polyamine moieties, wherein the polyamine moieties are bound to the biocompatible polymer, a plurality of nucleic acids electrostatically loaded onto the particles, a plurality of chemokine molecules, and a biodegradable polymer network, in which the loaded particles and chemokine molecules may be entrapped, are disclosed. Also disclosed is a method for treating a subject comprising administering a therapeutically effective dose of a pharmaceutical composition, the pharmaceutical composition comprising a particle composition that comprises a graft copolymer formed from a biocompatible polymer and a plurality of polyamine moieties, wherein the polyamine moieties are bound to the biocompatible polymer.

28 Claims, 16 Drawing Sheets

OTHER PUBLICATIONS

S.R. Little et al.; "Poly-β amino ester-containing microparticles enhance the activity of nonviral genetic vaccines"; Proc. Natl. Acad. Sci. USA, vol. 101, No. 26, pp. 6, 2004.

M. Peiser et al.; "CD1a and CDc cell sorting yields a homogeneous population of immature human Langerhans cells"; Journal of Immunological Methods, vol. 279, pp. 41-53, 2003.

H. Saeki et al.; "A migratory population of skin-derived dendric cells expresses CXCR5, responds to B lymphocyte chemoattractant in vitro, and co-localizes to B cell zones in lymph nodes in vitro"; European Journal of Immunology, vol. 30, pp. 2808-2814, 2000.

T. Kumamoto et al.; "Induction of tumor-specific protective immunity by in situ Langerhans cell vaccine"; Nature Biotechnology, vol. 20, pp. 64-69, 2002.

* cited by examiner (A)

A: Untreated Cells
B: Naked pDNA Treated cells
C: PLGA-PEI25kda Treated Cells
D: PLGA-PEI70kda Treated Cells (B)

POLYAMINE MODIFIED PARTICLES

RELATED APPLICATION

This application claims priority to U.S. provisional patent application No. 60/577,421, filed on Jun. 4, 2004, the full disclosures of which is incorporated herein by reference.

BACKGROUND

The present disclosure, according to one embodiment, relates to particle compositions modified with polyamines that may be used, among other things, in biomedical applications.

Microparticle-based delivery of nucleic acids has gained particular attention in recent years in view of improving the potency of DNA vaccination. Such improvement has been reported by encapsulation of plasmid DNA (pDNA) within biodegradable microparticles or through surface adsorption on cationic microparticles. However, the intrinsic intracellular barriers for gene delivery to antigen presenting cells (APCs) have not been adequately addressed in the rational design of delivery systems for DNA vaccines.

Nucleic acid-based immunotherapy could provide new treatment options for a variety of complex disorders including infectious diseases, allergies and cancers. They are also less expensive, easy to mass produce and potentially safer alternative to currently available live or attenuated vaccines. pDNA vaccination using polymer microspheres have shown improved potency and excellent promise for human applications. Traditionally, such formulations have involved encapsulating pDNA within the microspheres using emulsion-based techniques. Recently, it was reported that pDNA loaded on the surface of cationic microparticles might provide significantly improved immune response. Methods for synthesizing such cationic microspheres have involved cationic surfactants or physical blending of PEI or chitosan to PLGA particles.

It has been shown that pDNA encoding for particular antigens can generate long-term humoral and cellular immunity with efficient generation of CD4$^+$T helper cells and CD8$^+$ cytotoxic T cells in animal models. Specifically, DNA-based vaccines could have increased advantages over recombinant proteins and peptides in treatments of viral and parasitic infectious diseases as well as cancer whose resolution requires a strong CD8$^+$T cell-mediated cellular immune response and a Th1-mediated humoral response. Since the first demonstrations of the efficacy of pDNA as vaccines most clinical trials have focused on naked pDNA administration as the choice for delivery. Despite the widespread success of naked DNA in animal models, reproducible and robust clinical efficacy in human trials is yet to be demonstrated. In recent years, significant research has focused on developing effective delivery systems and adjuvants for improving the potency of pDNA-based vaccination including polymer-based particulate carriers, and novel immunomodulatory biomolecules (e.g. cytokines, CpG oligonucleotides, siRNA).

Biodegradable polymer microparticle-based delivery systems have shown an enhancement of efficacy for genetic vaccines. These particles are believed to possess intrinsic adjuvant activity by passively targeting dendritic cells due to their size (0.5-10 μm) and "foreign" composition. Two major microparticle-based delivery strategies have been pursued: either encapsulating the pDNA inside degradable microparticles or loading the anionic DNA on the surface of cationic particles. Although pDNA encapsulated within poly(lactide-coglycolide) (PLGA) microparticles has been studied, there exist some fundamental limitations to the approach including (a) low bioavailability of the DNA due to slow diffusional release, (b) low pH microenvironment created inside the particles during polymer degradation possibly compromising the bioactivity of pDNA, (c) limited encapsulation efficiency, and (d) confinement of the microparticles inside phagolysosomal compartments leading to inefficient transfection.

Surface loading of pDNA on cationic PLGA microparticles has shown significantly enhanced efficacy in animal models compared to naked DNA vaccines. This approach might have the advantage of (a) increased bioavailability, (b) improved loading efficiency, and (c) possible direct interaction of the bacterial CpG sequences in the plasmid with endosomal toll-like receptor 9 (TLR9) leading to better dendritic cell activation. However, current approaches to synthesize cationic microparticles have involved cationic surfactants or simple surface adsorption or blending of branched polyethyeleneimine (PEI) with PLGA, which rely on adsorption and physical entrapment of the cationic agent. This would likely suffer from pre-mature release of the molecules during formulation or prior to reaching the target cells leading to variable efficacy as well as undesirable cytotoxicity. Therefore, improved methods to present pDNA vaccines on particle surfaces along with design strategies for better dendritic cell transfection could improve the efficacy of DNA-based immunization.

Another significant advantage of particle-based delivery is that they can be potentially used for combinatorial DNA and protein/peptide immunization in a single dosage formulation. This ensures the ability to strategically modulate the immune responses against a given antigen and generate a balanced humoral and cellular immunity. Studies of adjuvant effects of polymer particles encapsulating a protein/peptide antigen have demonstrated that these particulate carriers are readily internalized by dendritic cell in culture, leading to expression of markers for dendritic cell maturation. In addition, by an as yet unknown mechanism, particulate delivery, at least for peptide immunization, increases the antigen presentation efficacy significantly.

Safe, yet effective adjuvants for vaccine applications are needed. Currently, aluminum salts (Alum) are the only FDA approved vaccine adjuvants in the US. However, its safety, efficacy and applicability in stimulating a balanced humoral and cellular immunity in a wide range of vaccines, especially genetic vaccines, are questionable.

SUMMARY

According to a specific embodiment of the present disclosure, particle compositions comprising a graft copolymer of a biocompatible polymer bound to plurality of polyamine moieties are provided. These particle compositions may further comprise one or more agents or one or more polymer networks, or both.

In general, the compositions of the present disclosure may display beneficial pharmaceutical properties and provides an opportunity for improvements in the delivery of drugs, vaccines, diagnostic agents, and nucleic acids. The compositions of the present disclosure may be used in a variety of applications, including, but not limited to combinatorial delivery (e.g., the co-delivery of nucleic acids and agents, such as therapeutic and diagnostic agents or imaging agents), therapies for cancer, prophylactic therapies (e.g., vaccinations) against diseases (e.g., parasite, bacterial, and viral mediated diseases), imaging, drug delivery, and tissue engineering.

According to a specific embodiment of the present disclosure, a chitosan graft copolymer particle composition comprising a chitosan moiety, or a derivative thereof, and a polyamine moiety, or a derivative thereof, grafted together by the use of an activated chitosan or polyamine species or both are provided.

According to a specific embodiment of the present disclosure, PEI surface functionalized PLGA microparticles (PEI-PLGA) are provided. Such compositions may be used as a delivery system with one or more of the following properties: (a) efficiently targets phagocytic cells (e.g. antigen presenting cells (APCs)), (b) remains non-toxic, among other things, because the attached PEI is surface immobilized in minimal quantities, (c) have intrinsic endosomal buffering and escape properties, among other things, due to the presence of secondary and tertiary amines on the surface, (d) allows efficient loading of nucleic acids, (e) allows codelivery of immunomodulatory molecules (e.g., cytokines, siRNA, oligonucleotides) encapsulated inside the particles, (f) increases pDNA bioavailability, and (g) may enhance cell maturation by allowing efficient activation of TLR9. The PEI-PLGA of the present disclosure may allow for better cell transfection and improved antigen presentation.

According to a specific embodiment of the present disclosure, combinatorial delivery polymers are provided that comprise a plurality of biocompatible particle compositions, according to a specific embodiment of the present disclosure, that comprises a graft copolymer of a biocompatible polymer bound to plurality of polyamine moieties; a plurality of nucleic acids electrostatically loaded onto the particles; a plurality of chemokine molecules; and a biodegradable polymer network, in which the loaded particles and chemokine molecules may be entrapped.

FIGURES

A more complete understanding of this disclosure may be acquired by referring to the following description taken in combination with the accompanying figures.

Figure 6:
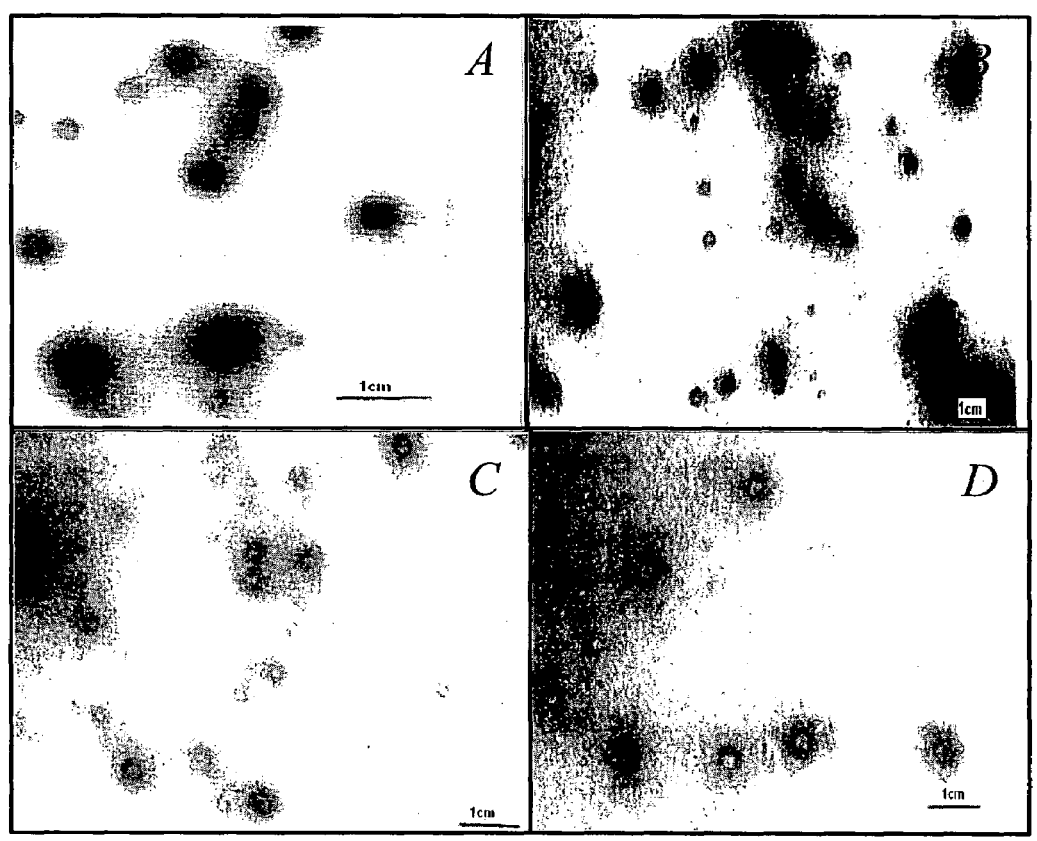

FIG. 6 is a transmission electron photomicrograph of nanocomplexes of (A) chitosan-g-PEI600/CMC with (wt/wt) ratios of 3.5:1; (B) chitosan-g-PEI600/CMC with (wt/wt) ratios of 7:1; (C) chitosan-g-PEI1200/CMC with the (wt/wt) ratios of 3.5:1; and (D) chitosan-g-PEI1200/CMC with the wt/wt ratios of 7:1; Scale 1 cm is equivalent to 208 nm, according to a specific example embodiment of the present disclosure.

Figure 7:
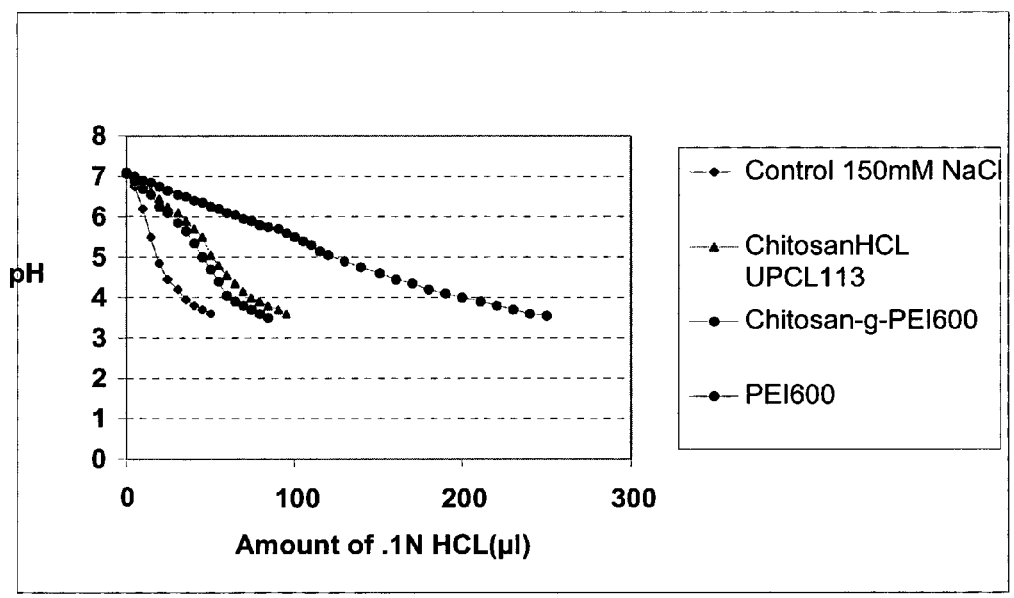

FIG. 7 is a graph showing the buffering ability of chitosan-g-PEI600, according to a specific example embodiment of the present disclosure.

Figure 8:
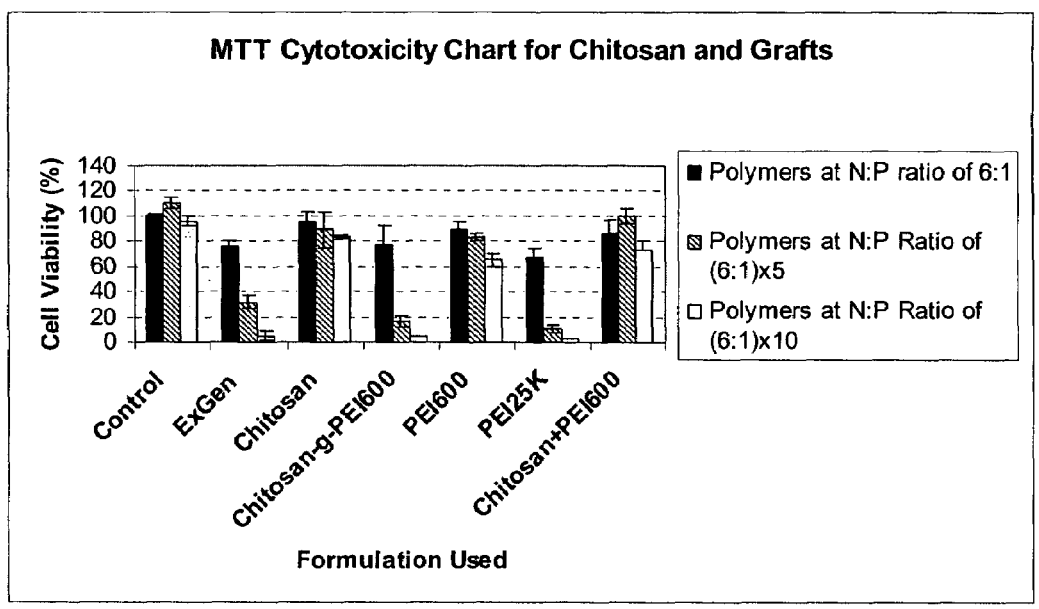
Figure 9:
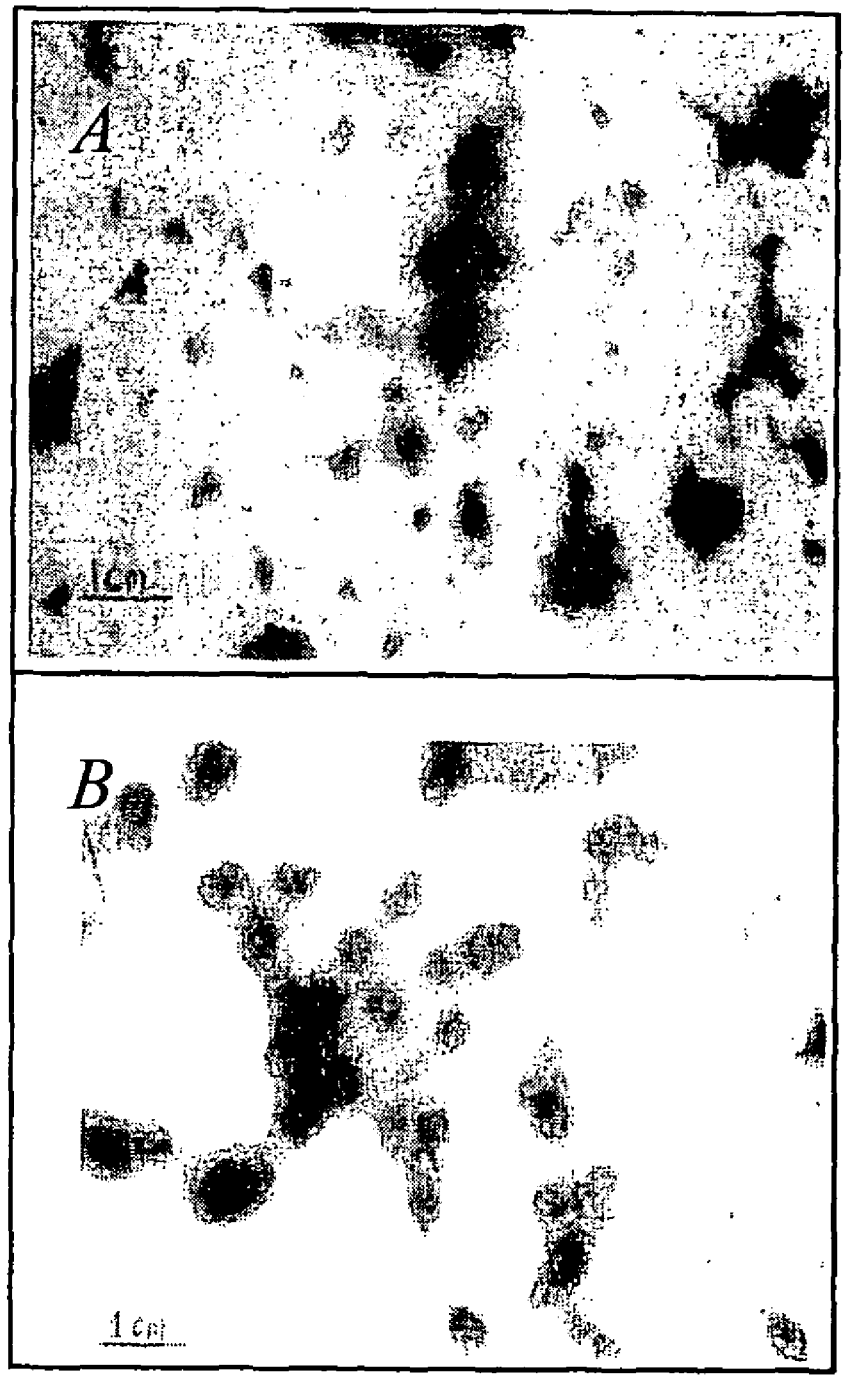

FIG. 8 is a is a graph showing the cytotoxicity for a chitosan-g-PEI, according to a specific example embodiment of the present disclosure FIG. 9 is a transmission electron photomicrograph of nanocomplexes of (A) chitosan/pDNA complexes at wt/wt ratio 5:1 in 5 mM sodium sulfate; (B) chitosan-g-PEI600/pDNA complexes at wt/wt ratio 5:1 in 5 mM sodium sulfate; Scale 1 cm is equivalent to 208 nm, according to a specific example embodiment of the present disclosure.

Figure 10:
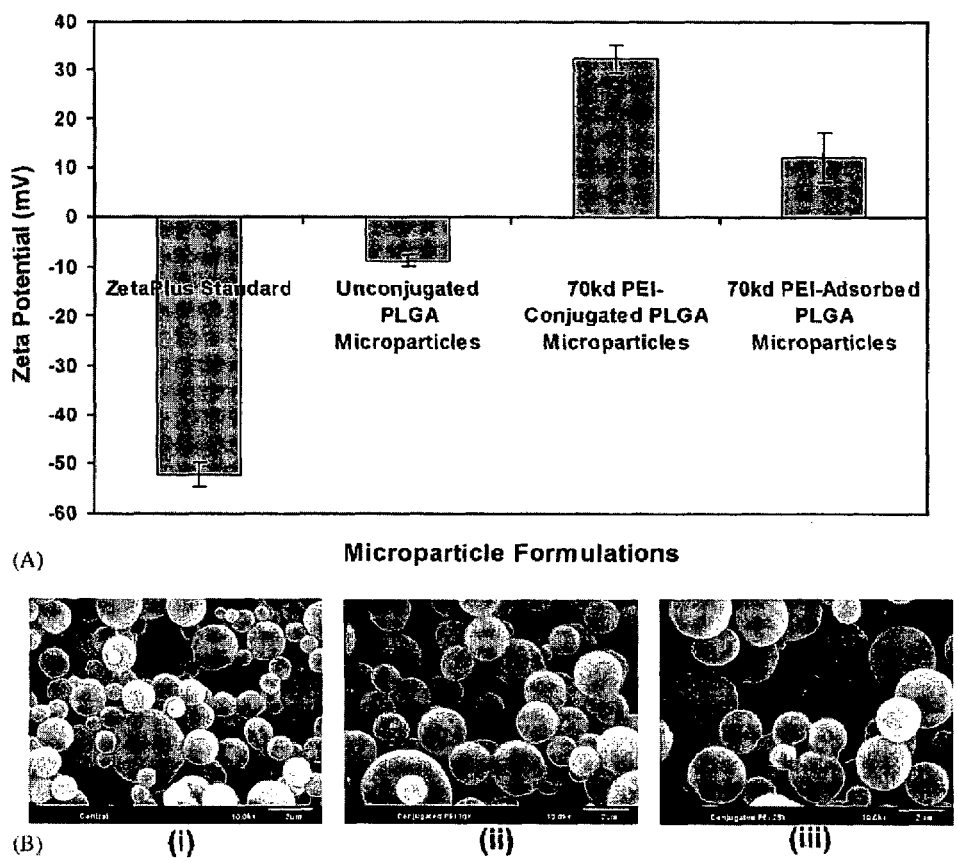

FIG. 10(A) is a graph of the zeta potential analysis of PEI-conjugated and adsorbed PLGA microparticles in comparison with unmodified particles, according to a specific example embodiment of the present disclosure.

FIG. 10(B) are scanning electron photomicrographs of (i) unmodified PLGA microparticles, (ii) PEI 70 k-conjugated PLGA microparticles and (iii) PEI 25 k-conjugated PLGA microparticles, according to a specific example embodiment of the present disclosure.

Figure 11:
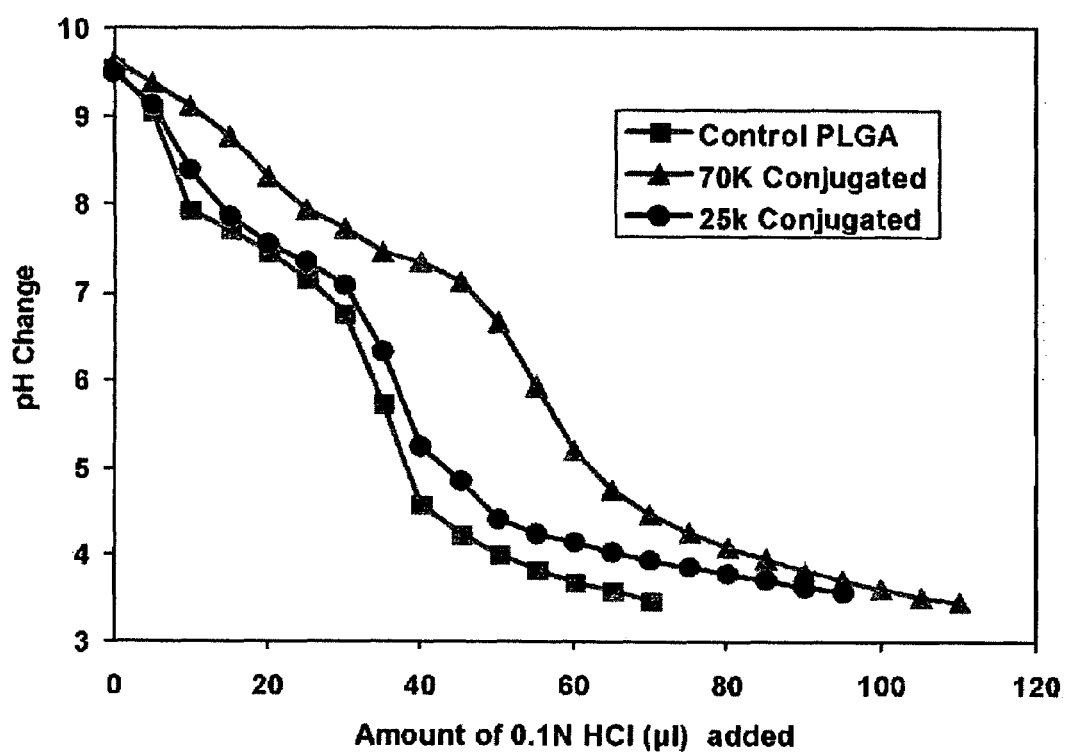

FIG. 11 is a graph of acid titration experiments with 0.1 N HCl to demonstrate the buffering ability of PEI-conjugated and unmodified PLGA microparticles, according to a specific example embodiment of the present disclosure.

Figure 12:
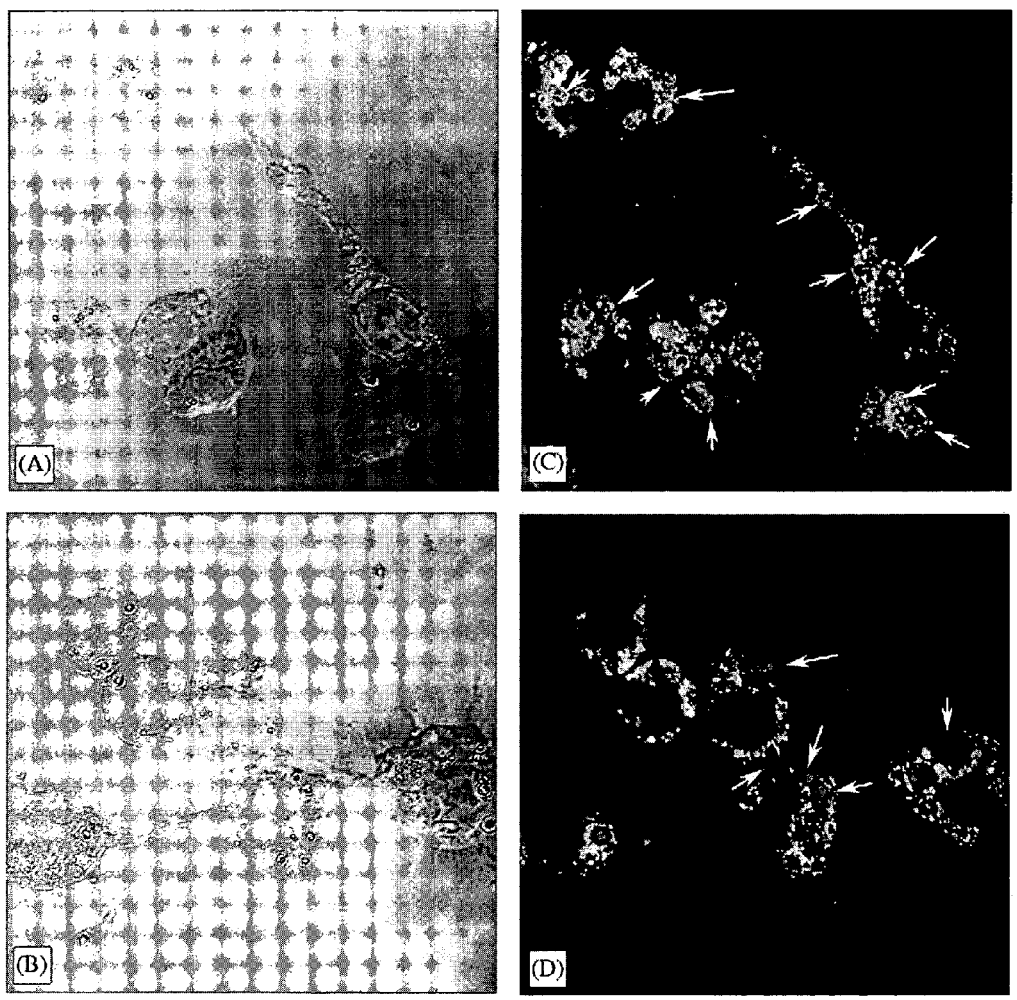

FIG. 12 are photomicrographs showing the uptake of dextran-rhodamine-encapsulated unmodified PLGA (A, B) and PEI 70 k-conjugated PLGA particles (C, D) in RAW 264.7 murine macrophage cells; (A) and (C) show differential interference contrast images and (B) and (D) show fluorescence images, according to a specific example embodiment of the present disclosure.

Figure 13:
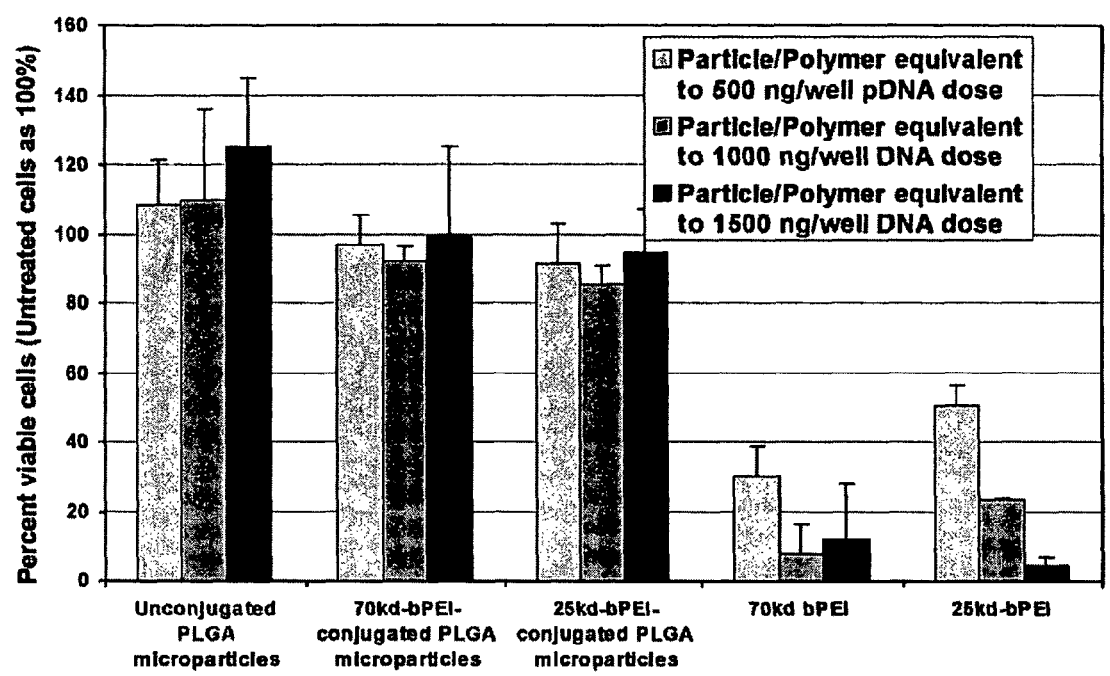
Figure 14:
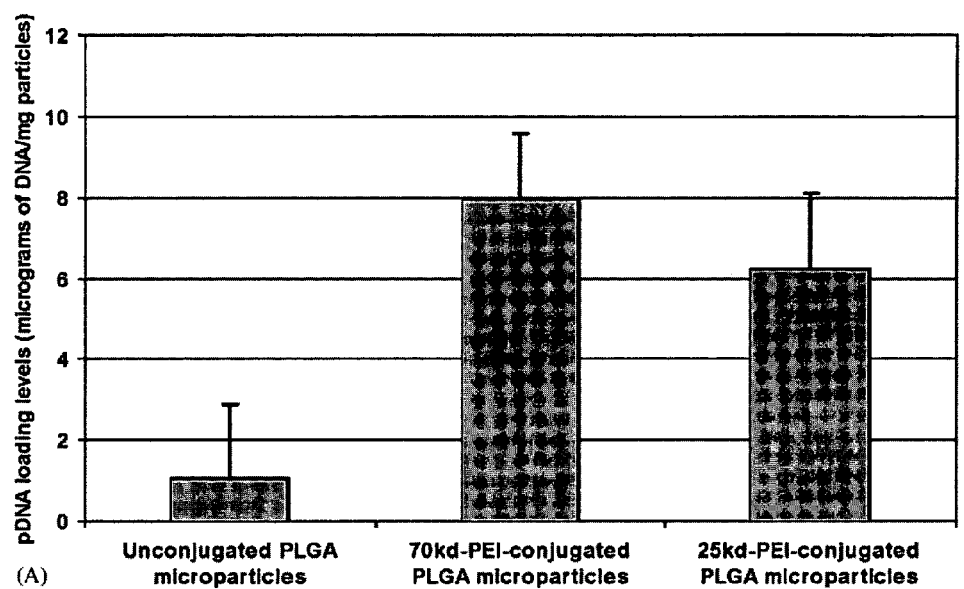
Figure 14:
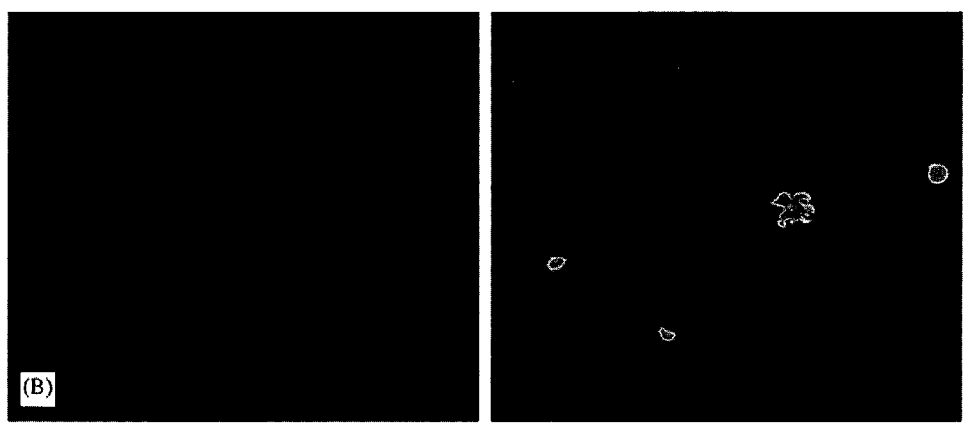

FIG. 13 is a graph showing cell viability in the presence of PEI-conjugated or unmodified PLGA microparticles (N=3 per group) after 24 hours of incubation; free PEI polymer was used for comparison, according to a specific example embodiment of the present disclosure, FIG. 14(A) is a graph showing pDNA loading levels on PEI-conjugated and unmodified PLGA microspheres, according to a specific example embodiment of the present disclosure.

FIG. 14(B) is a photomicrograph showing DAPI staining of pDNA adsorbed on PEI 70 k-conjugated microparticles and simultaneous staining of surface-loaded pDNA (DAPI) and co-encapsulated FITC-BSA on PEI 70 k-conjugated particles, according to a specific example embodiment of the present disclosure.

FIG. 15(A) is a photograph of a gel electrophoresis after transfection of RAW 264.7 murine macrophage cell lines with PEI 70 k- and PEI 25 k-conjugated PLGA microparticles using plasmid encoding for beta-galactosidase showing mRNA levels of beta-galactosidase 24 hours after transfection using RT-PCR, beta-actin was used as a house-keeping gene control, according to a specific example embodiment of the present disclosure.

Figure 15:
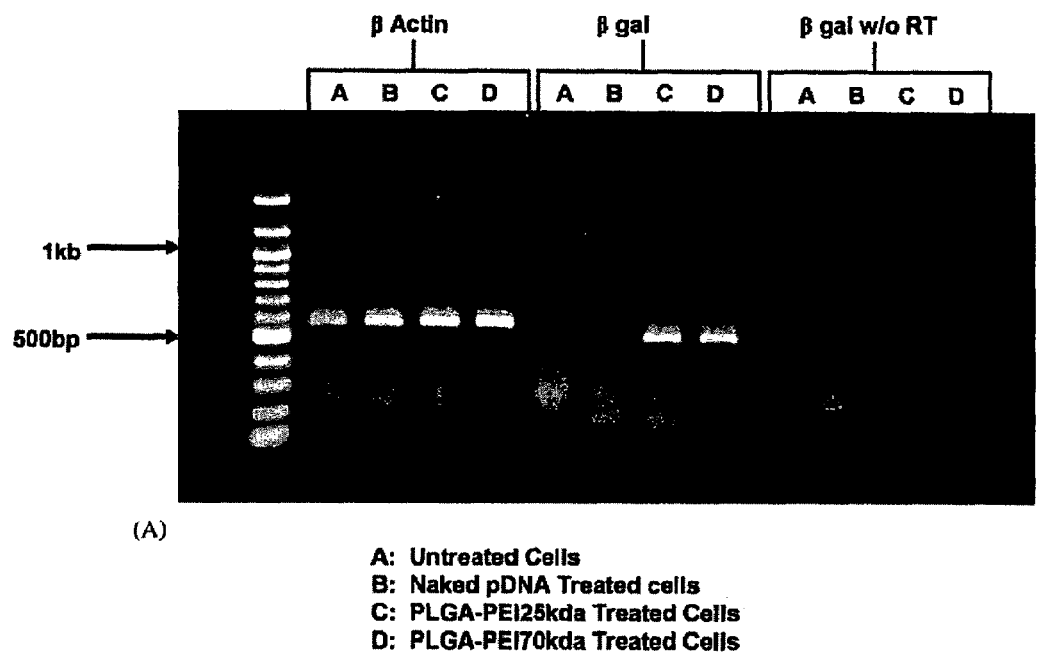
Figure 15:
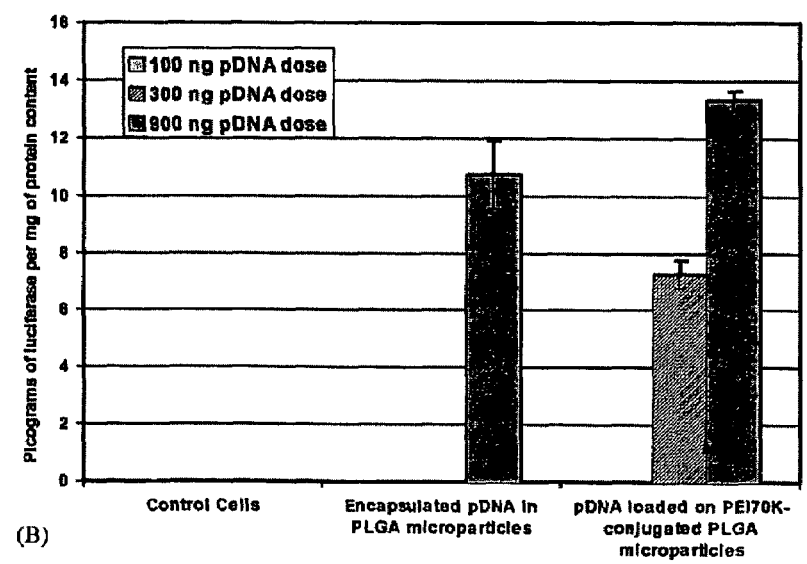

FIG. 15 (B) is a graph showing luciferase protein expression on RAW 264.7 murine macrophage cell lines following transfection with PEI-conjugated PLGA particles with surface-loaded pDNA or with pDNA encapsulated in PLGA particles, according to a specific example embodiment of the present disclosure; luciferase levels were measured 48 hours post transfection and normalized against total protein content measured using a BCA protein assay.

Figure 16:
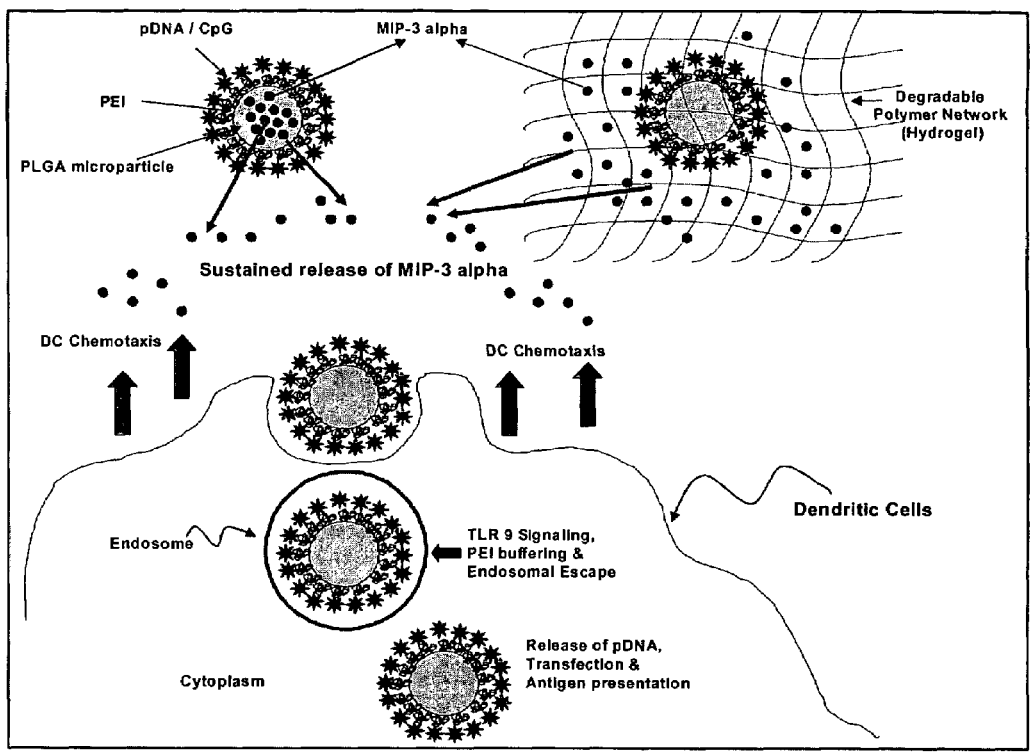

FIG. 16 is a schematic diagram showing the formulation of a vaccine, according to a specific example embodiment of the present disclosure.

The patent or application file contains at least one drawing executed in color. Copies of this patent or patent application publication with color drawing(s) will be provided by the Patent Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present disclosure provides, according to certain embodiments, particle compositions comprising a graft copolymer of a biocompatible polymer bound to a plurality of polyamine moieties. As used herein, "grafting" means a deposition technique whereby organic polymers can be bonded to a variety of other materials, both organic and inorganic, in the form of fibers, films, chips, particles, or other shapes. As used herein, "graft copolymers," or grammatical variations thereof, means a polymer having branches of varying length made up of different monomeric units on a common chain. Among other things, the polyamine moieties may enhance transfection of the particle. These particle compositions may further comprise one or more agents or one or more polymer networks, or both. The particle compositions should be of a size suitable for use in a subject (e.g., a human patient). The particles may have a size suitable for injection into a subject, such as a size in the micro or nano scale (e.g., microparticles or nanoparticles). They also may be biodegradable.

The polyamine moieties grafted to the particle may be any suitable polyamine moiety, or derivative thereof. In general, the polyamine moiety may be chosen so as to enhance transfection of the particle. The polyamine moiety should be bound to the particle by a covalent bond. Examples of suitable polyamines include, but are not limited to, polyethyleneimine (PEI), polyhistidine, putrescine, spermidine, and spermine.

Other agents may be associated with the particles. By associated, it is meant that the agent may be bound, attracted to, attached, trapped, or encapsulated by the particle. Examples of suitable agents include, but are not limited to, therapeutic agents, diagnostic agents, imaging agents, nucleic acids, pDNA, immunomodulatory molecules (e.g., cytokines, siRNA or CpG oligonucleotides), proteins, and peptides.

The biocompatible polymer suitable of use in the present disclosure generally should be capable of covalently binding a polyamine moiety. Examples of suitable particles include, but are not limited to, chitosan, a chitosan moiety, poly(lactide-coglycolide) (PLGA), and derivatives thereof.

The particle compositions may have a residual positive charge for certain applications, such as when the particle compositions is to interact with a drug or a biological membrane, to modify the tight junction of a mucosal surface, or to coat a negatively charged particle. The particle compositions may retain sufficient positive charge to allow it to interact with negatively charged (anionic) materials, such as oligonucleotides or nucleic acids (e.g., DNA), and provide for compaction of the anionic materials. Compaction, as used herein, should be understood to mean a reduction in particle size as measured by a technique such as atomic free microscopy or photon correlation spectroscopy. The particle compositions may have sufficient positive charge to allow it to interact with negatively charged colloidal carriers intended for drug delivery (e.g., emulsions, liposomes, microspheres, and microcapsules), as well as negatively charged drug particles having a size less than about 100 nm. The particle compositions may have a sufficient positive charge to interact with mucin or epithelial cells.

In drug targeting and drug delivery, as well as in diagnostic imaging and in the administration of vaccine systems, delivery materials in the form of emulsions, liposomes, microparticles, microcapsules, and nanoparticles may be employed. Such particles often carry a net negative charge. For some applications, it may be useful to modify this negative charge through, for example, the process of surface modification. Accordingly, in certain embodiments, the present disclosure provides the modification of such delivery materials with particulate compositions so that the delivery materials carry a positive charge to, among other things, provide for steric stabilization and beneficial biological and physical properties.

The particle compositions may be used to compact pDNA, which may have application in the field of gene therapy, among other things, because it is often important to be able to compact a plasmid material comprising nucleic acids into a small particle for improved administration. The resultant compacted product should have enhanced solubility and beneficial properties for the interaction with cells and for the subsequent expression of the gene product.

In some examples, the particle compositions may be further modified by the attachment of targeting ligands, for example, to the hydroxyl and unmodified amino functions. Such modification may provide, among other things, site specific targeting. Examples of suitable targeting ligands include, but are not limited to, sugars (e.g., mannose, fucose, and galactose) and proteins (e.g., monoclonal antibodies and fragments thereof). The specific sugar chosen may depend on, among other things, the nature of the tissue or cell that is identified as the target site. For example, a chitosan grafted copolymer particle composition (described below) complexed with DNA could be targeted to the liver by the covalent attachment of a triantennary galactose moiety.

A positive charge on the particle compositions may be evaluated by studying the interaction of the copolymer with a negatively charged polymer so that a polyelectrolyte complex is formed as described by Terayama in J. Polymer Science, 8:243 (1952). Alternatively, the particle compositions can be absorbed onto a polymer particle such as a polystyrene microsphere of about 1 micron in size and the charge on the system evaluated by particle microelectrophoresis using an apparatus such as the Malvern Zeta Sizer.

A sufficient positive charge for interacting with the above described anionic species typically refers to a charge, measured as the Zeta potential, of at least about 1 mV and preferably in the range of from about 1 to about 200 mV at about pH 7.4 in 1 mM HEPES buffer (or in 1 mM KCl).

The particle compositions or adducts may be prepared using techniques known in the art, and described herein, for bonding polyamine moieties to polymeric materials.

According to one embodiment, the present disclosure provides a chitosan grafted copolymer particle composition comprising a chitosan moiety, or a derivative thereof, and a polyamine moiety, or a derivative thereof, grafted together by the use of an activated chitosan or polyamine species or both. Chitosan grafted copolymer particle compositions in which the polyamine is PEI may be referred to as chitosan-g-PEI. The chitosan portion of the copolymer may have a molecular weight in the range of from about 10 kDa to about 1,000 kDa.

According to another embodiment, the present disclosure provides a chitosan grafted copolymer particle composition comprising a graft copolymer that comprises a chitosan moiety and a polyamine moiety (e.g., a PEI moiety), and a therapeutic agent, in which the therapeutic agent is formed from a plurality of nucleic acids (e.g., oligonucleotides). The polyamine moiety may be covalently bonded to the chitosan moiety and the therapeutic agent may be electrostatically loaded onto the particle.

Chitosan is a polymeric material comprising repeating monomeric units having the formula:

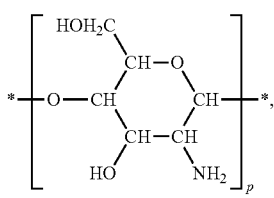

in which p is an integer and represents the number of monomeric units in the chitosan chain (i.e., the degree of polymerization).

In addition to the monomeric units shown above, chitosan will generally contain a proportion of the monomeric units found in chitin. This proportion will depend on the degree of deacetylation. Typically, the degree of deacetylation is in the range of from about 99% to about 10%, and may be in the range of from about 90% to about 20%, and may be in the range of from about 85% to about 40%.

The degree of conversion of the chitosan to the grafted copolymer form may be varied by controlling the chemical reaction used to form the bonds. In this regard, a range of chitosan grafted copolymer complexes for different pharmaceutical applications may be provided. For example, the polyamine (e.g., polyethyleneimine, PEI) or polyhistidine moiety may increase the solubility of the grafted copolymer, or the polyamine may increase the solubility of a grafted copolymer complexed with a therapeutic agent (e.g., a drug or a nucleic acid).

The amino ($NH_2$) or hydroxy (OH) or both may be converted within chitosan to the grafted copolymer form within the range of from about 1 to about 99%. In some examples, however, the conversion may be in the range of from about 10 to about 90%, and in other examples, in the range of from about 10 to about 50%. In general, not more than about 90% of the amine groups in chitosan should be bonded to provide the chitosan grafted copolymer with a sufficient positive charge. The person skilled in the art will be able to ascertain the degree of conversion necessary to meet the required pharmaceutical application.

Chitosan can be obtained in a range of molecular weights from oligomeric materials containing a few units of glucosamine through to higher molecular weight materials of more than 200,000 Da. In pharmaceutical applications, the higher molecular weights from about 50,000 to about 500,000 Da are normally preferred. Chitosan also may be obtained in different degrees of deacetylation. Chitosan having a deacetylation of between about 60 and about 90% may be preferred. Chitosan can be obtained from various sources, including shellfish, fungi, and other materials. A pharmaceutical grade of chitosan is commercially available from, for example, Pronova Limited of Norway.

The chitosans used for the preparation of the chitosan grafted copolymer can have a molecular weight in the range of from about 10 kDa to about 1,000 kDa, from about 10 kDa to about 500 kDa, for example, about 20 kDa to about 500 kDa, or from about 30 kDa to about 300 kDa, for example, between about 100 kDa and about 300 kDa.

The degree of polymerization of the chitosans used in the preparation of a chitosan grafted copolymer particle composition may be in the range of from about 50 to about 6,000, from about 100 to about 3,000, or from about 150 to about 2,000.

As mentioned above, chitosans that have been derived by modification of the hydroxyl function may be used. Such derivatives include O-acetylated and alkylated materials such as O-benzoyl chitosan and O-sulphated chitosans, as detailed in A. F. Roberts, *Chitin Chemistry*, Macmillan, 166 (1992). Thus, in the present disclosure, the chitosan moiety in a chitosan grafted copolymer particle composition may be chitosan, or a derivative thereof.

As mentioned above, the chitosan grafted copolymer particle compositions may be used to modify surfaces that are negatively charged, or to interact with or form complexes with negatively charged molecules such as DNA, pDNA, or nucleic acids. By way of explanation, and not of limitation, the positively charged chitosan of a chitosan grafted copolymer particle composition may strongly bind a negative surface, which may expose the polyamine group to the external environment. Such exposed polyamine groups may provide for steric stabilization. Such stabilization may, among other things, lead to an improved stability (e.g., for a colloidal dispersion) and have important biological implications in minimizing the uptake of proteins to the surface of a particle (e.g., when the particle is injected into the bloodstream or administered to a body compartment).

The chitosan grafted copolymer particle compositions may be prepared using techniques known in the art for bonding polyamine moieties to polymeric materials. For example, the PEI-chitosan copolymer may be prepared by a process comprising thiolation of chitosan using 2-iminothiolane. In a related aspect, thiolation of chitosan may be confirmed by using Ellman's assay. In another related aspect, polyamines may be separately made thiol reactive by using an NHS ester: maleimide heterobifunctional linkers. Such thiol reactive polyamines may be grafted on chitosan and evaluated qualitatively by, for example, FT-IR spectroscopy. In another example, A chitosan grafted copolymer particle composition may be synthesized using carboxymethylcellulose (CMC) as a counter-ion. In a related aspect, such particles may be characterized by, but not limited to, zeta potential measurement, size analysis, and transmission electron microscopy.

When used in drug delivery applications, the chitosan grafted copolymer particle compositions may provide advantageous properties, particularly in relation to the physiochemical properties of the chitosan material and the interaction of chitosan with surfaces, particles, and DNA. The chitosan grafted copolymer particle compositions of the present disclosure also may improve the paracellular transport of drugs as already described for chitosan itself. Moreover, the chitosan grafted copolymer particle compositions may be used to form controlled release materials in the form of microspheres, microparticles, and matrices for administration to the gastrointestinal tract, to the vaginal cavity, to the nose, and to the buccal cavity.

The chitosan grafted copolymer particle compositions also may be used for the administration of drugs to the eye wherein the chitosan would bind preferably to the mucus. In this regard, the chitosan grafted copolymer particle compositions may be used for the treatment of, for example, dry eye syndrome, in which the polyamine moiety provides a steric stabilization and lubricating effect. These products could be delivered to the eye using eye-drop systems known in the art.

The chitosan grafted copolymer particle compositions may complex with carbohydrates such as alginates, xanthans, dextran sulphate, and gellan. Accordingly, the chitosan grafted copolymer particle compositions may be useful for drug delivery applications. The chitosan grafted copolymer particle compositions also may interact with heparin and other negatively charged macromolecular drugs to form complexes. Nasal and vaginal products as liquids or powders based on the chitosan grafted copolymer particle compositions may be delivered by conventional devices such as spray pumps, powder insufflators, or syringes.

According to another embodiment, the present disclosure provides particle compositions comprising PEI surface functionalized PLGA particles (PEI-PLGA). The PEI covalently bound to the PLGA particle surface, which allows, among other things, efficient surface loading of nucleic acids, introduces intrinsic buffering properties to the resultant particle, and enhances transfection of phagocytic cells without affecting the cytocompatibility of PLGA carriers. Accordingly, PEI-PLGA particles may be capable of simultaneously delivering both DNA vaccines, as well as other immunomodulatory agents (e.g., cytokines or nucleic acids that are entrapped or encapsulated inside), within a single injectable delivery vehicle. Such compositions may be used in applications such as, for example, microparticle-based delivery of nucleic acids, proteins and peptides, and DNA vaccination. The combinatorial delivery polymers may be used to enhance the adjuvant effects of microparticles for genetic immunization and allow for safe yet highly efficacious vaccine formation.

In general, PEI is covalently bound to PLGA to form PEI-PLGA. Such covalent binding may be accomplished by covalently conjugating branched PEI or linear PEI using carbodiimide chemistry to the surface of PLGA. The resulting PEI-PLGA particle may be a cationic microparticle, which may then be complexed with an agent. The agent may be entrapped inside the PLGA matrix or presented on the surface or both. Examples of suitable agents include, but are not limited to, pDNA, immunomodulatory molecules (e.g., cytokines, siRNA or CpG oligonucleotides), proteins, peptides, and nucleic acids. For example, pDNA may be presented on the surface of a PEI-PLGA, while an immunomodulatory molecule may be incorporated inside the PLGA matrix. Surface presentation of pDNA may, among other things, allow for increased bioavailability from more efficient release of the pDNA (e.g., by competitive cationic (salt) interactions in the cytoplasm). Immunomodulatory molecules may, among other things, further aid in the process of crosstalk during the priming of naive T cells. Such complexed PEI-PLGA may be used for therapeutic or diagnostic delivery of the agent.

According to another embodiment, the present disclosure provides a combinatorial delivery polymer comprising a plurality of particles that comprise a graft copolymer of a biocompatible polymer bound to plurality of polyamine moieties, a plurality of nucleic acids electrostatically loaded onto the particles, a plurality of chemokine molecules, and a biodegradable polymer network in which the loaded particles and chemokine molecules may be entrapped. The combinatorial delivery polymer may be used in a variety of applications such as, for example, combinatorial delivery (e.g., the co-delivery of nucleic acids and chemokines and optionally other agents). Other applications include, for example, therapies for cancer, prophylactic therapies (e.g., vaccinations, such as nucleic acid vaccines) against diseases (e.g., parasite, bacterial, and viral mediated diseases), imaging, drug delivery, and tissue engineering. The particle may be a biodegradable, polymer particle surface modified to attach branched or linear polyamines, for example, a PEI-PLGA microparticle. The surface functionalization of PLGA microparticles using polyamines carrying secondary and tertiary amines (e.g., PEI) may enhance endosomal escape of the particles leading to increased transfection efficacy. Accordingly, covalent conjugation of branched and linear polyethyeleneimine on the particle surface using modified carbodiimide chemistry may be used to form the particle. Covalent conjugation, as opposed to simple adsorption, of the PEI may be important in certain applications because, among other things, free PEI may be cytotoxic and PEI is a highly hydrophilic molecule, which may diffuse out of the particle surface when placed in solution. Accordingly, certain examples of combinatorial delivery polymers, the amount of PEI is controlled to create a cationic particle surface and free PEI is minimized. Covalent conjugation also provides batch-to-batch reproducibility and a stable formulation by avoiding the inherent variability in the adsorption process.

Such PEI-PLGA microparticles are cationic, and may allow electrostatic loading of nucleic acids. Examples of nucleic acids that may be loaded on the particle include, but are not limited to, pDNA or CpG oligonucleotides, individually or in combination. Surface presentation of CpG oligonucleotides (e.g., as part of the plasmid backbone or in addition to the pDNA) on particulate carriers may allow for efficient activation of, for example, the toll-like receptor 9 (TLR-9) in the phagocytic pathway.

A plurality of chemokine molecules may be included in the combinatorial delivery polymer, or the chemokine molecules may be included in the particles (e.g., by encapsulation in the particles). As used herein, the term chemokine also refers to cytokines and chemo-attractants. Any chemokine molecule may be used. The specific chemokine chosen may depend on, among other things, the immunological requirements (e.g., the site of administration, antigen, target cells, and the like). Examples of suitable chemokine molecules include, but are not limited to, MIP-3$\beta$, MIP-3$\alpha$ (e.g., for cutaneous and mucosal Langerhans' cells), monocyte chemotactic proteins, for example, MCP-1 and MCP-3 (e.g., for intramuscular applications).

The plurality of chemokine molecules and the plurality of loaded particles are entrapped within the biodegradable polymer network. The biodegradability of the polymer network allows for efficient target cell migration and loaded particle uptake while releasing the chemokines at an optimum dose. Such a strategy creates a depot system for both chemokines and particles. This may, among other things, enhance the adjuvancy of the particle formulation, allow for more efficient delivery of the pDNA antigen, and ultimately augment the immune response in a subject.

The polymer network may be any polymer network capable of being injected into a subject and that is capable of gelling inside the tissue following injection. Any amount of chemokine may be entrapped within this network without loss of activity during the formulation process. The polymer network may be tuned to tailor the chemokine release profile for a desired application. One example of a suitable polymer network is an in situ crosslinking, biodegradable, hydrogel network, as described in Roy, et al., Mol Ther 7:401-8 (2003). Such polymer networks are based on chemical crosslinking between nucleophilic and an electrophilic PEG molecules that forms a network following administration thereby trapping any co-delivered biomolecule into a depot system. The network is also biodegradable due to the presence of a hydrolytically labile ester bond in the backbone of the PEG electrophile. Encapsulated molecules are released over time via diffusion and by continuing degradation of the network. Such a network is simple and injectable, made up of FDA approved, biocompatible polymers that can be easily scaled up and manufactured for clinical usage.

Combinatorial delivery polymers may be used to treat a subject (e.g., a human patient). By way of explanation, and not of limitation, a specific example embodiment of a combinatorial delivery polymer may operate as a vaccine as shown in FIG. 16. In this combinatorial delivery polymer sustained release of the chemokines from the hydrogel would attract naive (immature) dendritic cells to the site of administration and directly to the nucleic acid carrying microparticles. The particles, due to their inherent synthetic (foreign biomaterial) property and size (microns, resembling the size of pathogens), would be readily phagocytosed by the dendritic cell. Within the endosomal pathway, the surface adsorbed pDNA and CpG could interact with TLR-9 and initiate an NF-kB mediated response leading to activation and maturation of the dendritic cell. The availability of secondary and tertiary amines on the particle surface would enhance the buffering capacity of the particles and due to the proton sponge mechanism, could allow for more efficient endosomal escape. This would enhance pDNA delivery to the cytoplasm and increase transfection. Maturation of the dendritic cell would lead to migration to the secondary lymphoid organs where the expressed antigen will be presented to the T cells. Accordingly, some combinatorial delivery polymers of the present disclosure may be used, among other things, as a strong yet safe adjuvant leading to a stronger immune response against the pDNA encoded antigen.

Sustained release of chemokines from the polymer max enhance migration of immature Langerhans' cells to the injection site and lead to more efficient particle uptake and improved antigen presentation. Although bolus injection of MIP-3α along with the pDNA carrying microparticles might be effective, proteins and peptides are rapidly cleared away due to fast diffusion and degradation in tissues. The combinatorial delivery polymer, however, provides a sustained gradient of chemokines (e.g., MIP-3α), which may increase both the number of immature dendritic cells at the site of administration and the duration of their presence. An alternative design would be encapsulation of a chemokines inside the surface functionalized particles during their formation (e.g., during formation of the particles using a double emulsion process).

To facilitate a better understanding of the present invention, the following examples of specific embodiments are given. In no way should the following examples be read to limit or define the entire scope of the invention.

EXAMPLES

Example 1

An example of a chitosan-g-PEI and chitosan-g-PEI complex, according to a specific example embodiment of the present disclosure, was formed and studied as follows.

Materials and Methods.

Figure 1:
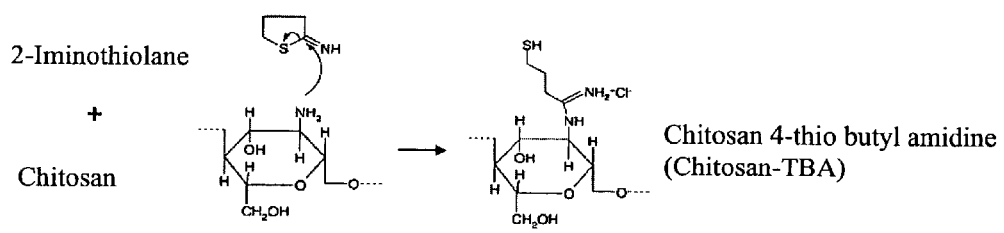
FIG. 1 is a schematic showing the thiolation of chitosan, according to a specific example embodiment of the present disclosure.

Preparation of PEI-chitosan Using Activated PEI: Chitosan Average MW ~250,000 Da, Vanson Polymers, WA) was thiolated using 2-Iminothiolane as shown in FIG. 1 and as described Cui, et al. Journal of Controlled Release 75:409-19 (2001), Constantia, et al. International Journal of Pharmaceutics 256:183-89 (2003), and Bernkop-Schnurch, et al., European Journal of Pharmaceutics and Biopharmaceutics, 57:9-17 (2004). Briefly, a 5% chitosan solution was adjusted to pH 6.5, to which 2-Iminothiolane was added in quantities of 0.5×, 1×, 2×, or 5× (SH:NH2). The reaction was allowed to proceed at room temperature under magnetic stirring for 24 hours. The resulting solution was dialyzed using 10 KDa MW Cut off for 2 days using 1% NaCl and 5 mM HCl to keep the pH low and prevent oxidation of sulfhydryls.

The resulting conjugates were lyophilized and stored under desiccation. Thiolation of chitosan was confirmed with an Ellman's assay using Ellman's reagent (5,5'-Dithio-bis-(2-nitrobenzoic acid), DTNB). Briefly, 50 µl of stock DTNB solution was diluted in 700 µl of 0.5M phosphate buffer pH 8.0 and added to 0.5 mg of hydrated chitosan and thiolated chitosan samples. The samples were centrifuged after reaction at room temperature for 2 hours, and the supernatant was read 450 nm and compared with standard curves established with thioglycolic acid with $r^2=0.9989$.

Figure 2:
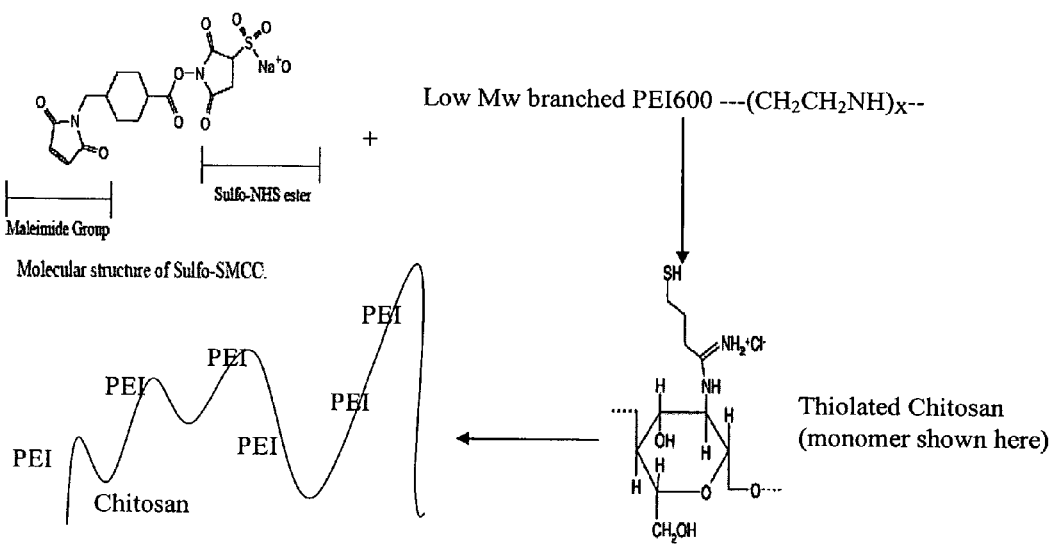
FIG. 2 is a schematic showing PEI grafting, according to a specific example embodiment of the present disclosure

PEI (MW 600 and 1200 Da, Polysciences Inc., PA) was separately made thiol reactive by using water-soluble analogs of NHS ester:maleimide heterobifunctional linkers reacted together at room temperature for about 1 hour. Control batches had thiolated chitosan with PEI600 without crosslinker during the process of grafting. This thiol reactive PEI (crosslinker activated PEI600) was then reacted overnight with the sulfhydryl modified chitosan to form the graft (chitosan-g-PEI). FIG. 2 shows a schematic of PEI grafting. All batches were dialyzed alike to remove nongrafted, excess PEI molecules using Snake Skin Dialyzer (MW cutoff 3.5 KDa, Pierce Biotechnology Inc., IL) for 2 days using 1% NaCl and 5 mM HCl to keep the pH low and prevent oxidation of sulfhydryls. The resulting conjugates were lyophilized and stored under desiccation until further analysis.

Thiolation of chitosan was confirmed with an Ellman's assay. Briefly, 5 mg of control chitosan, thiolated chitosan, and PEI grafted chitosan were hydrated in 250 µl of deionized water, and 50 µl of stock DTNB solution was diluted in 700 µl of 0.5M phosphate buffer pH 8.0 and added to the hydrated samples. The samples were centrifuged after reaction at room temperature for 2 hours, and the supernatant was read at 450 nm and compared with standard curves established with thioglycolic acid with $r^2=0.9974$.

Lyophilized grafts were used for FT-IR studies. FT-IR experiments were done using KBr pellets made by homogenously mixing 2 mg of chitosan, sulfhydryl modified chitosan and the PEI grafted chitosan with 300 mg of KBr. FT-IR spectra were recorded using plain KBr pellets for background subtraction using 32 interferograms with 4 cm resolution on a Nicolet Magna IR-560 FT-IR Spectrophotometer.

Complexes were synthesized using a simple technique as described in Mize Benis, et al., Gene Therapy 7:2105-12 (2000) using a chitosan (or chitosan-g-PEI)/CMC (wt/wt) ratios of 3.5:1. Transmission Electron Micrographs were taken on a Philips 208 TEM. The particle sizing and Zeta Potential Analysis were performed using a Zeta Plus Analyzer (BrookHaven Instruments, Holtsville, N.Y.).

Buffering ability of chitosan-g-PEI: The ability of chitosan-g-PEI to resist acidification was tested using acid titration assay as described in Tang, et al., Gene Ther 4(8):823-32 (1997). Briefly, 10 mg/mL of lypholyzed chitosan-g-PEI was suspended in 150 mM NaCl. The pH was first adjusted to 9.0 and then titrated in small increments with 0.1 N HCl until a pH of 3.5 was reached. The slope of the pH versus HCL added graph provides an indication of the intrinsic buffering capability of the chitosan-g-PEI.

Cytotoxicity evaluation for chitosan-g-PEI: Preliminary toxicity evaluations of chitosan-g-PEI were conducted in comparison with commercially available transfection agents and unmodified chitosan. Cytotoxicity evaluation was conducted by incubating cells with free polymers in 1×, 5×, and 10× concentrations higher than that needed for transfection (N:P ratio of 6:1 was chosen). An MTT (3-[4,5-dimethylthiazol-2-yl]-2,5-diphenyl tetrazolium bromide) assay was used to evaluate the cytotoxicity of cationic microparticles. Twenty thousand RAW murine macrophage cells were seeded on tissue-culture-treated 96-well plates and cultured overnight. Cells were incubated with the formulations for 24 hours, rinsed with PBS, and cytotoxicity was evaluated using MTT according to the manufacturer's protocol with untreated cells as negative control. Cell viability was conducted by comparing the amount of MTT utilized by live cell mitochondrial dehyrogenases to produce formazan crystals which are solubilized using acidified isopropanol and absorbance readings were taken on a microplate spectrophotometer at 570 nm.

Results.

Figure 3:
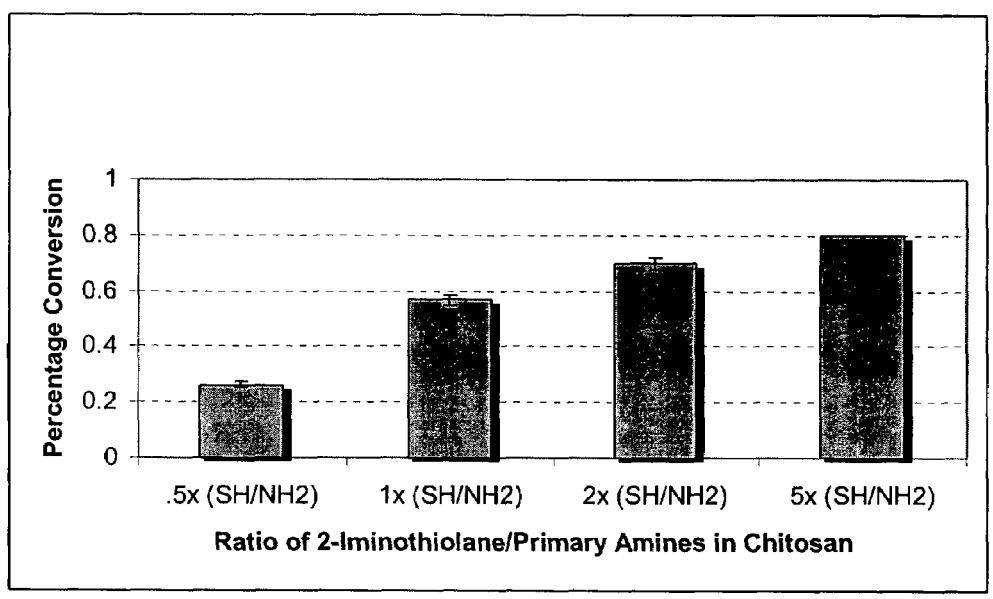
FIG. 3 is a graph showing the thiolation of chitosan with increasing amounts of 2-Iminothiolane, according to a specific example embodiment of the present disclosure.
Figure 4:
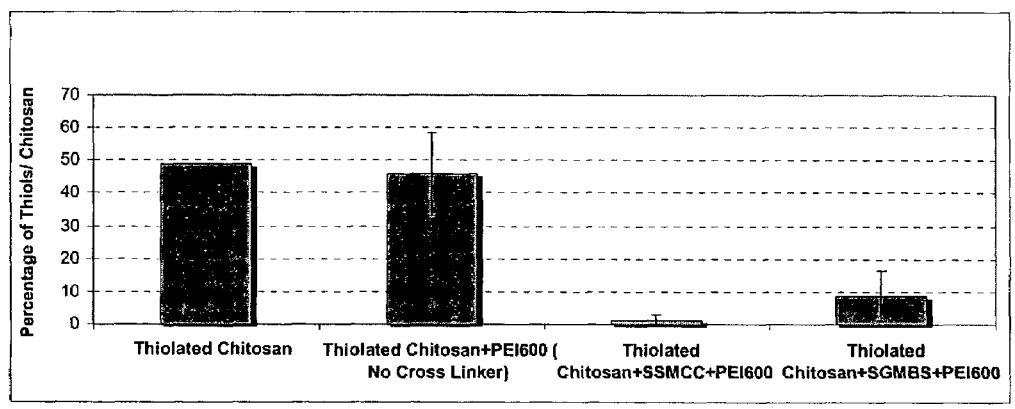
FIG. 4 is a graph showing the reduction in thiolation after PEI grafting, according to a specific example embodiment of the present disclosure.
Figure 5:
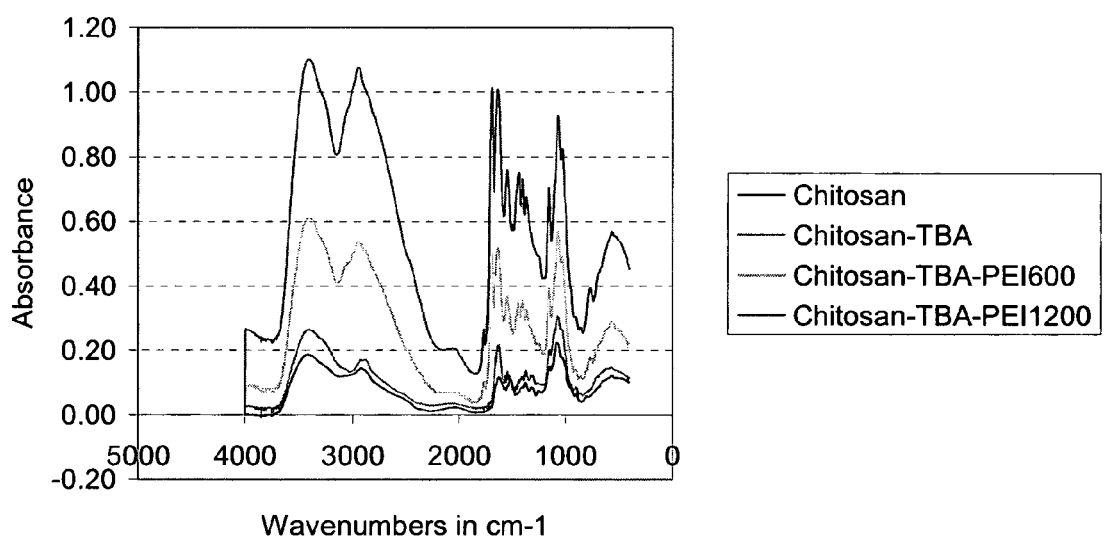
FIG. 5 is an FT-IR spectra of chitosan, chitosan-Trauts, chitosan-g-PEI600, and chitosan-g-PEI1200, according to a specific example embodiment of the present disclosure.

Thiolation of Chitosan: 2-Iminothiolane successfully converted ~24% of the primary amine groups in the backbone of chitosan to carry a free sulfhydryl group (FIG. 3 and FIG. 4). Thiol quantification by Ellman's assay was done with standard curves established using thioglycolic acid. Statistical analysis on the reproducibility of thiolation was done using ANOVA. Statistical significance between the controls and the samples were established using a one tailed t-test ($P<0.01$).

FTIR Spectra of PEI grafting on Thiolated Chitosan: PEI grafting can be indicated from the FT-IR spectra of unmodified chitosan and chitosan-g-PEI (FIG. 6), which indicates the appearance of a doublet peak at 1600. Such peaks are indicative of the presence of secondary amines in the grafted polymer. Since chitosan does not carry any secondary amine groups, it is a signature of the presence of PEI. Furthermore, the increase in carbonyl stretching indicates the presence of a thioester linkage formed between SH and maleimide. Also seen is the relative increase in the height of the carbonyl stretching and NH bending peaks in the PEI grafted polymer compared to the height of the C—O peak seen at 1075 in the control samples. Relative changes in the heights of the peaks at $CH_2$ stretching at 2900 in comparison with the OH stretching which is consistent in the PEI grafted chitosan's and significantly smaller in the control chitosan samples.

Nanocomplexes formed by Complex Coacervation with CMC: FIG. 7 shows that nanocomplexes formed with Chitosan-g-PEI are similar in appearance with unmodified Chitosan complexes.

Sizing and Zeta Potential: chitosan-g-PEI nanocomplexes showed an increase in the mean size of particles with increasing molecular weight of the grafted PEI. In addition, the zeta potential of particles formulated with these graft copolymers are significantly higher indicating the presence of highly charged branched PEI on the surface as shown in Table 1.

TABLE 1

| Type of Complex (wt/wt) | Size (nm) | Zeta Potential in mV |
|---|---|---|
| 3.5:1 Chitosan/CMC | 192.15 +/− 3.46 | 47.35 +/− 4.78 |
| 3.5:1 Chitosan-g-PEI600/CMC | 284.65 +/− 30.33 | 59.91 +/− 0.438406 |
| 3.5:1 Chitosan-g-PEI1200/CMC | 328.3 +/− 115.117 | 76.285 +/− 0.502046 |

Buffering ability of chitosan-g-PEI: Weight analysis of the lyophilized grafts indicated a three fold increase for the grafted polymers compared to the controls post grafting. Considering that equal weights of the chitosan and chitosan-g-PEI were used in titration it could be estimated that the graft carrying an equivalent weight of chitosan in addition to the grafted PEI would have thrice the buffering ability (FIG. 8).

Cytotoxicity evaluation for chitosan-g-PEI: As shown in FIG. 8, chitosan-g-PEI was found to be considerably toxic at 5× and 10× concentrations in comparison with unmodified chitosan, while chitosan and PEI600 incubated with cells did not prove toxic suggesting possible toxicity issues of either thiolated chitosan or the crosslinker.

Example 2

In order to demonstrate the difference between the compaction of DNA with chitosan and the compaction of DNA with an example of a chitosan-g-PEI, according to one embodiment of the present disclosure, a model plasmid material can be employed. This may be in the form of a plasmid such as CMV-CAT (pCAT) that encodes for chloramphenicol acetyl transferase (CAT), a so-called reporter gene system, commercially available from Gene Medicine, Inc., Houston, USA, or pgWiz Luciferase, commercially available from Aldevron LLC., ND.

Complexes were synthesized using a simple technique as described in Mize Benis, et al., Gene Therapy 7:2105-12 (2000) using a chitosan (or chitosan-g-PEI)/CMC (wt/wt) ratios of 3.5:1. The pCAT-DNA/chitosan or the pCAT-DNA/chitosan-g-PEI complexes is prepared to give different pCAT-DNA/polymer ratios. The size of chitosan and PEI-chitosan complexes and their zeta potentials in water and 1 mM HEPES buffer at pH 7.4 is determined using a Malvern S4700 PCS and a Malvern Zeta Sizer (Mark IV) (or a ZetaPlus machine (BrookHaven Instruments Corp., NY)), respectively. Transmission Electron Micrographs were taken on a Philips 208 TEM.

FIG. 9 shows that nanocomplexes formed with chitosan-g-PEI are similar in appearance with unmodified chitosan complexes (compare to FIG. 6). The size and zeta potentials are shown in Table 2 (compare to Table 1).

TABLE 2

| Type of Complex (wt/wt) | Size (nm) | Zeta Potential in mV |
|---|---|---|
| Chitosan-g-PEI600/pDNA | 262 ± 20.35 | 31.67 ± 1.28 |
| Chitosan/pDNA | 292.3 ± 52 | N/A |

It will be appreciated by those skilled in the art that the size of the resulting complexes between plasmid DNA and a compacting polymer will be affected by the ratio of the interacting components and the processing conditions.

Example 3

An example PEI-PLGA and PEI-PLGA complex, according to one embodiment of the present disclosure, was formed and studied as follows.

Materials and methods.

Polymers and Reagents: PLGA RG502H (Boehringer Ingelheim, VA (I.V=0.16-0.2 dL/g, MW ~11,000 Da), Poly (vinyl alcohol) MW ~31,000 (88% hydrolyzed) was purchased from Fluka. Branched PEI, MW=~70,000 Da was from Poly-sciences Inc., PA, and MW=~25,000 Da was from Sigma Aldrich, MO. Rhodamine conjugated Dextran (MW ~70,000 Da), Streptavidin-FITC, and DAPI Nuclear Stain were obtained from Molecular Probes, OR. Plasmids pgWiz Luciferase and pgWiz β-galactosidase were from Aldevron LLC., ND. Anti-LAMP-1 antibody and Goat Anti Rat IgG2a-biotin was purchased from Pharmingen (BD BioSciences), CA.

Cell lines and cell culture products: RAW 264.7 murine macrophage cell line was obtained from American Type Culture Collection (ATCC, VA). ATTC-modified DMEM were used to maintain these cells. All other reagents for cell culture were purchased from Invitrogen, CA.

Synthesis of water-in-oil-in-water (w/o/w) emulsion microparticles: PLGA microparticles were synthesized using a w/o/w double emulsion, solvent evaporation technique. Briefly, 0.35 g of acid end-terminated PLGA was dissolved in 7 mL of methylene chloride (EMD Chemicals, NJ). 300 µL of deionized water was added to this polymer solution and homogenized at 10,000 rpm for 2 minutes using a Silverson SL2 T homogenizer (USA). This primary emulsion was poured into 50 mL of 1% PVA solution and homogenized for 1 minute to obtain a w/o/w emulsion followed by solvent evaporation for 3 hours. Microparticles formed were washed 3 times with deionized water, lyophilized and stored at −20° C. The particles were further characterized with respect to size, zeta potential (ZetaPlus, BrookHaven Instruments, NY) and by scanning electron microscopy (SEM, Philips 515). Fluorescent microparticles were synthesized using dextran-rhodamine in the internal aqueous phase (1 mg/mL in water) and remaining steps were unaltered. FITC conjugated BSA (Sigma Aldrich, St Louis, Mo.) was also incorporated in the primary emulsion during the process of particle synthesis followed by surface modification with PEI as described below. pDNA encapsulated in PLGA microparticles were synthesized as previously described by McKeever, et al. Vaccine 20(11-12): 1524-31 (2002) and Roy, et al. In: Fifth Cold Spring Harbor conference on gene therapy, Sep. 25-29, 2000, New York: Cold Spring Harbor Laboratory.

Synthesis of cationic microparticles: A modified EDC (1-ethyl-3-(3-dimethylaminopropyl)carbodiimide hydrochloride)/NHS chemistry was used to conjugate PEI to the surface of PLGA microspheres to obtain cationic microparticles. Briefly, 20 mg of PLGA microparticles was suspended in 800 mL of 0.1 M MES (2-(N-morpholino) ethane sulfonic acid) buffer, pH 5.1. EDC (Pierce Biotechnology Inc., IL) and water soluble sulfo N-hydroxysuccinimide (Sulfo NHS) (Pierce Biotechnology Inc.) in 40 molar excess were dissolved in ice cold 0.1 M 2-Morpholinoethane-sulfonic acid (MES) buffer and added dropwise to the PLGA particle suspension. EDC activation was done for 2 hours at room temperature. Five molar excess of 70 kDa branched PEI (Polysciences Inc., PA) or 15 molar excess of 25 kDa branched PEI (Aldrich, Wis.) was diluted in 9 mL of 0.1 M MES buffer. Activated PLGA microparticles were added dropwise to the PEI solution with magnetic stirring and incubated for another 2 hours at room temperature. PEI-conjugated microparticles were washed 4× in excess 1 M NaCl to remove physically adsorbed PEI and the resulting microparticles were lyophilized and stored at 20° C. Fluorescent cationic microparticles were synthesized by conjugating PEI (70 or 25 kDa) to the surface of dextran-rhodamine-entrapped PLGA microparticles. FITC-BSA entrapped PLGA-PEI particles were synthesized similarly and used for pDNA loading and confocal studies. PEI-adsorbed particles were synthesized as described above except for EDC-NHS activation.

Fluorescamine assay for quantification of PEI: Fluorescamine (4-phenylspiro[furan-2(3H), 1'-phthalan]-3,3'-dione) has been used for colorimetric quantification of primary amines and to quantify PEI associated with microparticles. PEI-conjugated microparticles were hydrolyzed in 0.1 N NaOH overnight and the PEI content was measured using spectro-fluorometric analysis. Fluorescamine reacts with primary amines in PEI to form pyrrolinones, which is excited at 390 nm and has emission peak at 475-490 nm. PEI amounts (w/w) in microparticles were estimated using standard curves of PEI. All measurements were performed on a Fluoroplate Reader (BioTek, Vermont).

Buffering ability of PEI-conjugated PLGA microparticles: Ability of PEI-conjugated PLGA microparticles to resist acidification was tested using acid titration assay as described above.

Cytotoxicity evaluation using MTT assay: MTT assay was used to evaluate the cytotoxicity of cationic microparticles as described above. Briefly, twenty thousand RAW murine macrophage cells were seeded on tissue-culture-treated 96-well plates and cultured overnight. Micro-particle formulations were added at doses of 0.25, 0.5, and 1.0 mg/mL in 0.2 mL of complete cell culture medium. The concentrations of polymeric particles were chosen from an estimated pDNA loading of 10 μg/mg and an equivalent pDNA dose of 500, 1000 and 2000 ng/well. The PEI polymer amounts used were for equivalent amount of pDNA dose using a 9:1 N:P ratio. Cells were incubated with the formulations for 24 hours, rinsed with PBS, and cytotoxicity was evaluated using MTT according to the manufacturer's protocol with untreated cells as negative control.

Confocal microscopy: In order to confirm the increased buffering ability noticed using acid titration experiments, confocal microscopy was used to study cell uptake and phago-somal trafficking. RAW murine macrophage cell line was used as a model phagocytic system. $0.5 \times 10^6$ cells were seeded overnight on fibronectin (Sigma Aldrich, MO)-coated glass coverslips. Dextran-rhodamine-entrapped unmodified PLGA or PEI-modified PLGA microparticles were added to the wells at 50 mg/mL and incubated for 4-6 hours at 37° C. Cells were fixed with 4% paraformaldehyde for 30 minutes and permeated using 0.2% Triton X-100 (Avocado Chemicals, MA). Fixed and permeated cells were blocked with 1% BSA and a rat antimouse CD107a (LAMP-1) (Pharmingen, BD Biosciences, CA) antibody was used to stain lysosomes followed by biotinylated Goat anti Rat IgG2a and Streptavidin-FITC. Nuclei were counterstained with DAPI and controls were performed to evaluate background staining with the secondary antibody and the Streptavidin-FITC but without any primary anti LAMP-1 antibodies. Cells were imaged using a LEICA Confocal Laser Scanning Microscope with a 63× oil immersion objective.

Plasmid DNA loading on cationic microparticles: pgWiz Luciferase was loaded on the surface of cationic microparticles as described in Singh, et al. Proc Natl Acad Sci USA 97(2):811-6 (2000). Briefly, pDNA loading was attempted at 1% w/w by incubating pDNA with the cationic microparticle suspension in PBS, pH adjusted to 6.5, at 4° C. for 6 hours. pDNA was also adsorbed on control (unmodified) PLGA microparticles using the same conditions as for the cationic particles. The resulting particles were centrifuged at 12,000 rpm for 15 minutes on a microcentrifuge and washed 2× with the loading buffer. The supernatant was collected and analyzed spectrophotometrically (A260 nm) for pDNA content. pDNA loading on the cationic microparticles was calculated by subtracting the pDNA content in the supernatant from the initial concentration of pDNA added. In addition, pDNA loading was also analyzed directly by hydrolyzing the DNA-adsorbed particles overnight in 0.1 N NaOH and evaluating the DNA concentration spectrophotometrically. The total pDNA calculated both by direct and indirect methods were in concurrence.

Evaluation of transgene mRNA levels in RAW murine macrophage cell lines using RT-PCR: For RT-PCR evaluation, RAW cells were seeded at 0.5×106 cells/mL in six-well plates. Untreated cells were chosen as negative controls. Comparative studies were performed using 3 μg of pgWiz β-galactosidase adsorbed on 70 or 25 kDa PEI-modified cationic PLGA microparticles. Following 24 hours incubation in complete serum medium, cells were rinsed and lysed using Trizol® (Invitrogen, CA) and stored at 80° C. before isolation of total RNA. Total RNA was isolated using chloroform phase separation/ethanol precipitation and reconstituted in DEPC-treated water (Invitrogen, CA). RT-PCR (AccessQuick™ RT-PCR System, Pro-mega, WI) of the total RNA was performed using a β-gal specific 500 bp amplicon (Applied Biosystems, CA). Housekeeping gene β-actin was chosen as a positive control using a 573 bp primer (Invitrogen, CA). RT enzyme free samples were used as DNA contamination control. All PCR reactions were performed using standard PCR conditions.

Evaluation of luciferase expression in RAW cells: 5×104 cells were seeded in 96-well tissue culture treated plates (Costar, Fischer Scientific). Microparticle formulations with pgWiz Luciferase DNA adsorbed were added at pDNA equivalent doses of 100, 300 and 900 ng/well in triplicates. For comparisons with encapsulated formulations, pDNA was encapsulated as previously described. Cells were incubated with these formulations, in complete serum medium, for 48 hours at 37° C., washed with sterile PBS, lysed using the Glo Lysis Buffer (Promega, WI) and lysates divided equally for luciferase content and total protein content analysis. Luciferase was assayed (Dynex Plate Reading Luminometer) using the Bright Glo Luciferase Assay System (Promega, WI) according to manufacturer's protocol. Total protein content was determined using a Micro BCA protein assay kit (Pierce Biotechnology, IL). The luciferase content obtained from the luminescence readings was normalized to the total protein content.

Statistical analysis: Single Factor ANOVA was used for unequal variances to establish significant between the adsorbed and the conjugated batches and a P<0.05 was considered to be significant.

Results

Covalent conjugation is a reproducible method for fabricating highly cationic, biodegradable microparticles: PEI was successfully conjugated on the surface of PLGA microparticles using a simple, EDC-NHS chemistry. Surface modification was characterized by zeta potential analysis while conjugation of PEI was quantified using a fluorescamine assay. As shown in FIG. 10A, PEI-modified particles show significantly positive zeta potential indicating a positively charged surface. Unmodified particles exhibit a negative zeta potential arising from the surface carboxyl groups. It is evident that covalent conjugation yields a significantly higher zeta potential (+35 mV) compared to simple surface adsorption of PEI (+10 to 24 mV). In addition, our results from multiple experiments (data not shown) suggest that the adsorption process is highly variable and poorly reproducible. On the other hand, the conjugation process produces a fairly reproducible charged surface. Fluorescamine quantification of PEI indicated that the amounts of PEI present on particle surface are 6.5 μg for PEI 70 kDa and 5-6 μg for PEI 25 kDa per microgram of microparticles. SEM analysis of PEI-conjugated and unconjugated particles indicate no significant change in surface morphology (FIG. 10B). These results indicate that covalent conjugation of PEI on the surface of biodegradable PLGA microparticles produces highly reproducible cationic particles with minimal amount of PEI present on the particle surface.

PEI conjugation imparts buffering properties to PLGA microparticles: We hypothesized that covalent surface modification of PLGA particles with branched polyamines carrying secondary and tertiary amines might enhance endolysosomal pH buffering which could lead to increased phagosomal escape of the carrier particles (proton sponge mechanism). The buffering capacity of PEI-conjugated particles was assessed by measuring the change in pH of a particle suspension (10 mg/mL) upon addition of increasing amounts of 0.1 N HCl. As shown in FIG. 11, significant buffering ability is imparted on PLGA particles upon conjugation of PEI, especially with the 70 kDa molecular weight PEI. This is indicated by the shift and a decrease in the slope of the titration curve.

Surface functionalization of PLGA microparticles allows early phagosomal escape: The intracellular distribution of unmodified and PEI-conjugated, dextran-rhodamine-entrapped PLGA microparticles were evaluated by confocal fluorescence microscopy. FIG. 12 shows that as early as 4-6 hours posttransfection, significant numbers of 70 kDa PEI-grafted microparticles were in the cytoplasm while high number of the unmodified particles (red) appears to be associated with or surrounded by the LAMP-1 molecules (green), indicating phagolysosomal presence. This supports the hypothesis that PEI conjugation on the surface of PLGA microparticles could lead to their preferential escape from the endolysosomal compartments. We did not see a significant portion of the PEI 25 kDa conjugated PLGA microparticles free from localization with phagosomes. This data supports the buffering experiment conducted which clearly indicated that the PEI 70 kDa imparts significantly higher buffering when compared to the PEI 25 kDa branched PEI. Taken together, the results from FIG. 11 and FIG. 12 indicate that PEI conjugation likely enhances pDNA delivery into the cytosol and should lead to more efficient transfection of dendritic cells.

Covalent conjugation of PEI to PLGA particles produces non-cytotoxic delivery vehicles: In vitro cytotoxicity was evaluated using RAW macrophage cells with increasing doses of PEI-micro-particle concentrations (0.25, 0.5 and 1 mg/mL) as well as with free PEI in doses equivalent for delivery of same amounts of pDNA to cells. These concentrations of polymeric particles were chosen from an estimated pDNA loading of 10 μg/mg and an equivalent pDNA dose of 500, 1000 and 2000 ng/well. The PEI amounts were for equivalent amount of pDNA dose using a 9:1 N:P ratio. As shown in FIG. 13, PEI-conjugated PLGA microparticles were nontoxic in comparison with free PEI. This demonstrates that covalent immobilization on a solid surface could effectively minimize the toxicity of PEI molecules.

pDNA can be efficiently loaded on surface-modified PLGA microspheres: As shown in FIG. 14(A), efficient surface loading of pDNA was achieved in PEI-conjugated PLGA particles. PEI 70 k-conjugated particles showed an average loading of 8 μg pDNA/mg of formulation while PEI 25 k-conjugated particles had an average loading of 6 μg/mg. The target loading being 1% w/w, the loading efficiency was 70-90% for PEI 70 k and 50-80% for PEI 25 k. The loading was confirmed by both direct and indirect assays as described above.

pDNA and model proteins can be simultaneously delivered using PEI-conjugated particles: FIG. 14(B) demonstrates that multiple biomolecules can be delivered simultaneously to the same cell using the proposed formulation. FITC-labeled BSA was encapsulated within PLGA microparticles during the double emulsion process followed by surface conjugation of PEI. Following pDNA loading, the microparticles were stained with DAPI and visualized under confocal microscope. As shown, coloading of both pDNA (left and right image, blue staining) and FITC-BSA (right image, green staining) was successfully achieved using the surface functionalized particles.

PEI-grafted PLGA microparticles efficiently transfect phagocytic cells: Total RNA from pgWiz β-galactosidase DNA treated murine cells were isolated 24 hours posttransfection. Transfection was conducted in full (serum containing) culture medium. As illustrated in FIG. 15(A), beta gal amplicon was detected only for the RNA extracts from cells treated with the PEI-conjugated PLGA microparticles carrying the pDNA. Negative controls with no RT enzyme showed no pDNA contamination. Beta Actin expression (house keeping gene) was used as a positive control. It is evident from the result that efficient transfection of phagocytic cells can be achieved within 24 hours of incubation using cationic microparticles.

Quantification of luciferase protein expression in phagocytic cells with 300 and 900 ng/well dose of pDNA adsorbed on PEI-conjugated PLGA microparticles were determined. RAW macrophage cells were successfully transfected as detected by luminescence activity in picograms/milligram of total protein content (FIG. 15(B)). However, using pDNA-encapsulated PLGA particle treated cells for comparison, we failed to detect any luciferase activity in the 300 ng dose level. Although the encapsulated-pDNA formulations generate significant immune response in vivo and in clinical trials, minimal or no transgene expression is detected in vitro at low DNA doses. This could possibly be attributed to the delayed release kinetics and low bioavailability of the pDNA from encapsulated formulations.

Example 4

An example of a combinatorial delivery polymer, according to one embodiment of the present disclosure, may be formed and studied as follows.

Preparation of Surface-Modified Biodegradable Particles on which pDNA and CpG oligonucleotides can be loaded and evaluate their ability to enhance dendritic cell transformation.

Synthesis of PLGA microparticles: PLGA microparticles will be prepared as described above.

PEI conjugation: As described above, an optimized carbodiimide chemistry will be used to conjugate either branched or linear PEI to the surface COOH groups of acid-capped PLGA microparticles. Briefly, 20 mg of PLGA microparticles will be suspended in 800 µl of 0.1 M MES (2-(N-morpholino) ethane sulfonic acid) buffer (pH 5). EDC and water soluble sulfo-NHS ester (>25 molar excess of the weight of PLGA) will be added to the PLGA particle suspension for 2 hours at room temperature. 5 molar excess of bPEI (70 kDa, PA, 25 kDa, Aldrich, Milwaukee, Wis.) or 3 molar excess of linear PEI would be diluted in 14 mL of 0.1M MES buffer pH 6.5 and reacted with the activated PLGA microparticles for 3 hours at room temperature. The PEI conjugated microparticles will be washed 4× in 1M NaCl to remove physically adsorbed PEI. The resulting microparticles will be lyophilized and stored at −20° C. until further use.

Particle characterization: Surface functionalization with PEI will be verified using a variety of analytical techniques, as described above.

Zeta potential: Zeta potential is an indirect estimation of the surface charge by estimating the shear or stern layer potential of the electrokinetic unit formed when microparticles are suspended in a salt solution. Zeta potential analysis would be done as describe above. Briefly, 100 µl of a 1 µg/mL suspension of PLGA microparticles, with and without PEI conjugated to the surface, would be diluted in 1 mM KCL. Readings will be taken in duplicate runs (5 each time) for the same sample and averaged.

Sizing Using Dynamic Laser Light Scattering (DLLS): The microparticles synthesized would be sized using DLLS (BrookHaven Instruments, Holtsville, N.Y.). Briefly, 1 µg/mL suspension of PLGA microparticles would be diluted 1:3 and readings would be taken at a temperature of 25° C. with a scattering angle of 90° C. for 120 seconds. The number average distributions of sizes would be obtained using the NNLS algorithm incorporated in the ZetaPlus software.

SEM and TEM: Scanning and transmission electron microscopy will be used to analyze particle morphology. Briefly, for TEM, a dilute suspension of PLGA microparticles would be air dried on 200 mesh carbon coated copper grids. 1% uranyl acetate would be used for negative staining of particles. For SEM, particles will be deposited on double sided carbon tapes and sputter coated with 60/40, gold/palladium before imaging.

Fourier Transform Infrared Spectroscopy (FT-IR): In order to confirm the presence of branched PEI and linear PEI on the surface of the microspheres, FT-IR would be used to investigate the presence of surface amine groups. Briefly, freeze dried surface modified PLGA microparticles would be mixed with FT-IR grade Potassium Bromide (Sigma Aldrich) with a ratio of 1:150 mg. KBr Pellets would be read immediately using a Nicolet Magna IR-560 FT-IR spectrophotometer. The readings would be taken at 4 $cm^{-1}$ resolution with 100 scans per sample. The FT-IR spectra would be analyzed for stretching and bending peaks of the primary and secondary amines in the backbone of the conjugated PEI.

Fluorescamine Assay for Quantification of PEI: Fluorescamine is a well established reagent that has been used for calorimetric quantification of primary amines and has been used to quantify PEI associated with microparticles. Branched PEI conjugated microparticles would be dissolved in 0.1N NaOH and used for measuring the PEI content by spectrofluorometric analysis. Fluorescamine reacts with primary amines in PEI to form a colored product which is excited at 390 nm and has an emission peak at 475-490 nm. PEI amounts wt/wt of PLGA microparticles would be estimated using standard curves of stock branched PEI.

Nucleic acid loading on cationic microparticles: pDNA or CpG oligonucleotide adsorption would be conducted using an overcompensation loading technique. Briefly, 2.5 mg of surface-functionalized microparticles would be suspended in 0.5 mL of PBS (pH adjusted to 6.0 to ensure protonation of the surface amine groups). 37.5 µg of pDNA (pgWiz-HBsAg, Aldevron LLC, ND) alone or 19 µg of pDNA and 19 µg CpG ODN (5'TCCATGACGTTCCTGACGTT-3', Oligos Etc. OR) (SEQ ID NO:1), would be suspended together in 0.5 mL of PBS pH 6.0. The microparticle suspension would then be added drop wise using a 27 1/2 G insulin syringe (Beckton and Dickinson, USA) to the pDNA solution under mild vortexing. The nucleic acid loading would be continued on an end to end shaker for 12 hours at 4° C. The loaded microparticles would be separated by centrifugation and used for further analysis and use.

Analysis of nucleic acid loading: Microparticles loaded with only pDNA would be analyzed using both direct and indirect spectrophotometric approaches. In the indirect method, supernatants after each wash during pDNA loading would be collected and analyzed for DNA content by absorbance readings at 260 nm on a UV-VIS spectrophotometer (Beckmann DU-530 Life Science, Single Cell Module). pDNA loading on the microparticles are calculated by subtracting the pDNA content in the supernatant from the amount added initially. For direct estimation of pDNA loading on the microparticles, the DNA-loaded microparticles would be dissolved in 0.1N NaOH. The resulting solution would be analyzed for pDNA content using absorbance readings at 260 nm and using PicoGreen fluorometric estimation (Molecular Probes, OR)

Simultaneous-loading of pDNA and CpG oligo on same microparticle surface will be analyzed by HPLC using methods previously developed as described in Roy, et al., Mol Ther 7:401-8 (2003). Briefly, nucleic acid loaded particles will be dissolved in 1N NaOH. The resulting sample will be subjected to HPLC separation using a DNA-NPR (Tosoh-Biosep Inc.) anion exchange column with a gradient elution (Buffer A: 0.56 M sodium chloride in 50 mM Tris, pH 9.0; Buffer B: 1.2 M sodium chloride in 50 mM Tris, pH 9.0; 0-30% Buffer B in 15 minutes). A standard curve will constructed with the input pDNA and CpG oligonucleotide diluted in PBS at various concentrations.

Does PEI-PLGA particles enhance dendritic cell transfection?: As shown above in Example 3, we have demonstrated that PLGA-PEI microparticles can efficiently transfect phagocytic cells using both mRNA and protein expression assays. The transfection efficacy of these particles further may be evaluated using bone marrow derived dendritic cells (BMDCs) and the therapeutic hepatitis B surface antigen (HBsAg) plasmid (pgWiz-HBsAg, Aldevron LLC, ND).

Formulate nucleic acid-loaded particles along with the dendritic cell chemo-attractant MIP-3α in an injectable, biodegradable polymer network and evaluate dendritic cell chemo-attraction, migration, and activation using in vitro and in vivo models.

MIP-3α is a well characterized chemokine for cutaneous and mucosal Langerhans' cells as well as $CD34^+$ HPC derived APCs. It is a ligand for CCR6, a cell surface receptor primarily expressed in immature Langerhans' cells. It is upregulated in inflamed or damaged epithelium, leading to migration of immature and precursor Langerhans' cells at the site leading to antigen loading. MIP-3α is a direct mediator of Langerhans' cells chemotaxis and hence is a rational choice for this cutaneous formulation.

BMDCs will be generated from bone marrow cells of 4-8 weeks old BALB/c mice as previously described in Lutz, et al. J Immunol Methods 223:77-92 (1999). Briefly, marrow will be isolated using sterile techniques from the tibia and femur of euthanized mice. Bone marrow cells will be cultured at 2×105 cells/mL with 10 mL in a 100 mm bacterial petri dish. Granulocyte monocyte colony stimulating factor (GM-CSF) would be added at 20 ng/mL on day 0, 3 and day 6. On day 7 immature dendritic cell would be isolated using magnetic separation (Dynabeads™ (Dynal Biotech) labeled with CD11c antibody (Ebiosciences, CA)), and used in subsequent assays. PLGA-PEI particles will be directly compared for gene delivery and protein expression efficacy with PLGA and pDNA encapsulated PLGA microparticles, two existing particle-based formulations for delivery of DNA vaccines. These particles will be synthesized according to published protocols. p pgWiz-HBsAg (Aldevron Inc.) will be adsorbed on PLGA-PEI and PLGA-CTAB particles or encapsulated in unmodified PLGA microparticles as described before. Equal pDNA doses will be added to each well of BMDC cells. Cells will be analyzed for mRNA levels of HBsAg using quantitative RT-PCR (Invitrogen) at various intervals (1, 2, and 3 days) after transfection according to manufacturer's protocol.

Can PEI-functionalized PLGA particles, carrying surface pDNA/CpG activate immature dendritic cell?: Activation of immature dendritic cell with various microparticle-based formulations will be evaluated using a method described in Little, et al. Proc Natl Acad Sci USA 101:9534-9 (2004). Primary BMDCs (isolated as described before) will be cultured at $1\times10^6$ cells/well in six-well plates. A suspension of different microparticle formulations (50 μg/well) will be added to the culture medium and incubated for 24 hours. PLGA-PEI (branched) with or without surface-loaded pDNA, PLGA-PEI (linear) with or without surface-loaded pDNA, PLGA-PEI surface loaded with both pDNA and CpG oligonucleotides, pDNA encapsulated PLGA microparticles and PLGA-CTAB microparticles with surface loaded pDNA will be used. Untreated cells will be used as negative controls while LPS (100 ng/mL, Sigma) will be used as positive control for dendritic cell activation. After 24 hours, cells will be stained with antibodies against F4/80, mCD40, mCD86, mCD80, and m41BBL (e-Bioscience, CA) at 4° C. for 30 minutes and analyzed with a FACScan flow cytometer (Becton Dickinson). Increase in expression of various surface markers (and decrease in F4/80) will be used as evidence for dendritic cell activation.

In-situ crosslinking polymer networks and in vitro release studies: We propose a degradable depot system that is easy to fabricate, cost effective and could be highly efficacious in Langerhans' cell attraction and activation. Briefly a 3% w/v solution of hydrolytically degradable tetra-functional PEG-SH (sulfhydryl) and PEG-malaemide (custom synthesized from Nektar Therapeutics, AL) will be formulated in PBS. These polymers are chosen to avoid cross-reactivity with the MIP-3α itself during hydrogel formation since all members of the known chemokines have cysteine's in the disulphide forms without any free reduced SH. pDNA loaded microparticles along with soluble MIP-3α will be suspended in the PEG-SH phase. The amount of MIP-3α in the hydrogel would be optimized based on subsequent in vitro and in vivo assays. Immediately prior to administration, the PEG-SH/microparticle/MIP-3α formulation will be mixed with the PEG-malemide solution to ensure PEG crosslinking and hydrogel formation. Detailed physico-chemical studies on similar systems described in Roy, et al. Mol Ther 7:401-8 (2003), have shown the kinetics of gelation and have demonstrated that such a formulation is injectable and act as a slow release depot system with tunable release kinetics. This crosslinking formulation will be used for in vitro and in vivo studies of Langerhans' cell activation and antigen presentation as well as for parallel studies on immune response.

The release kinetics of MIP-3α from the polymer network and the degradation behavior of the hydrogel should be characterized in order to understand the process of chemo-attraction and particle uptake. In order to evaluate MIP-3α release from the crosslinked 3% network, hydrogels with soluble MIP-3α will be pre-formed at 37° C. in microfuge tubes (in triplicates) with various initial amounts of the chemokine (10, 20, 50, 100 and 500 ng). 1 mL of PBS will be added to the tubes, followed by incubation at 37° C. At various time points (1 hr, 1 d, 3 d, 5 d, 7 d, 10 d, 14 d, 21 d) 200 μL of the buffer solution will be retrieved and replaced with fresh buffer. Amount of MIP-3α released would be analyzed using the murine CCL20 immunoassay kit (R&D Systems, MN., Catalog Number MCC200) according to the manufacturer's protocol. Briefly, 50 μl of sample would be added to the ELISA plates (pre coated with capture antibody towards MIP-3α) containing 50 μl of the assay diluent and incubated for 2 hours. Detection would be performed using 100 μl of MIP-3α detection antibody/enzyme conjugate followed by addition of 100 μl of tetramethyl benzidine (TMB) substrate. The reaction will be quenched by adding an 0.1N HCL stop solution and the plates would be read using a Dynatech absorbance plate reader at 450 nm using 570 nm as the reference filter.

Evaluating dendritic cell migration-Transwell chamber model: Since our target cell population in vivo are immature epidermal Langerhans' cells, we propose to use Langerhans' cells directly isolated from mouse skin to quantitatively evaluate cell migration in response to sustained release of MIP-3α from the cross linked polymer networks. Immature Langerhans' cells will be isolated obtained from mouse ears by a method similar to that described in, Peiser, et al., J Immunol Methods 279:41-53 (2003) and Saeki, et al. Eur J Immunol 30:2808-14 (2000), using magnetic separation. Briefly, skin from BALB/c (4-8 weeks old) mice will be surgically removed, incubated in dispase I (Roche, 18 hour, 4° C.) to remove the dermal layer followed by preparation of cell suspension in 0.25% trypsin (37° C., 15 minutes) along with vigorous pipetting and passage through a 40 μm cell strainer. Langerhans' cells will be isolated using a rat anti-mouse Cd1a antibody (Pharmingen) conjugated to magnetic microbeads (Dynabeads, Dynal Biotech)).

Chemotaxis assays will be performed as detailed in Kumamoto, et al. Nat Biotechnol 20:64-9 (2002). Transwell chambers (6.5 mm, Costar, Cambridge, Mass.) with a pore size of 5 μm will be used to study migration of Langerhans' cells. Crosslinked hydrogels, as described in the previous section, will be loaded with various amounts of MIP-3α (0, 3, 10, 30, 60, 100 and 300 ng). The hydrogels will be placed at the bottom of the Transwell chamber and dendritic cell will be added to the filter unit. At various time points after incubation (2 h, 6 h, 12 h, 1 d, 3 d, 5 d) migratory cells will be harvested from the lower chambers and counted using flow cytometry for CD11c+ cells. The percentage of dendritic cell migrated will be calculated by dividing the number of CD 11c+ cells collected from the bottom chamber by the total CD11c+ cells initially added to the upper chamber. A migration kinetics curve plotting cumulative number of migrated dendritic cell versus time will be used to evaluate optimal MIP-3α dose. The dose at which the largest number of Langerhans' cells migrate into the bottom well will be used for further in vivo studies.

Evaluating Langerhans' cell attraction and activation: Skin model: In order to test our hypothesis that sustained release of MIP-3α can attract epidermal Langerhans' cells and increase microparticle delivery to Langerhans' cells, we propose to use an in vivo Langerhans' cell activation assay using murine ear skin as a model system and evaluate whether the polymer-formulations containing MIP-3α induces efficient Langerhans' cell migration to the pDNA carrying microparticles and increases particle uptake. Formulations (microparticle/MIP-3α or polymer networks carrying particle and soluble MIP-3α will be injected into the ear of BALB/c mice (4-8 weeks old). All microparticles will be loaded with pDNA and stained as detailed in the previous section. The ear tissue will be excised at various time points (10 min, 30 min, 1 hr, 3 hrs, 6 hrs, 12 hrs and 24 hrs) followed by epidermal sheet preparation an dendritic cell staining with the I-A antibody, as described in Gu, et al., J. Drug Del. Sci. Tech 14:265-273 (2004). Particle-Langerhans' cell localization and particle uptake by Langerhans' cells will be evaluated using confocal microscopy (Leica) of epidermal sheets. We plan to use concentrations of MIP-3α optimized through the in vitro experiments described in the previous section. However, we would also vary the MIP-3α concentration around this optimized amount in order to reconfirm that we have arrived at an optimal formulation that can be used for immunization studies.

For quantitative comparison, each confocal z-series sections with fluorescently immunostained dendritic cells and fluorescently labeled pDNA carrying particles will be analyzed. Dendritic cell migration (and chemo-attraction) will be evaluated by manually counting the number of cells present in a given field of view using a 10× objective. The data will be summed over all z-section for a specific field of view and expressed as total number of cells per field. This will be repeated over 10 random fields of view around the site of injection and the average number of particles per field will be used as a quantitative measure of dendritic cell migration. Graphs indicating number of cells/field plotted against time (minutes after formulation administration), as shown in the preliminary data section, will be used to evaluate the kinetics and magnitude of dendritic cell migration. Since we also expect that epidermal Langerhans' cells will phagocytose the particles, get activated and emigrate from the tissue to the local lymphnode, we can plot number of cells/field over time and evaluate both Langerhans' cell attraction and activation (i.e. migration away from the site following particle ingestion).

We expect that compared to particle formulations carrying no MIP-3α, MIP-3α coencapsulated with particles in the network formulation will have enhanced Langerhans' cell migration leading to increased particle delivery to Langerhans' cells. Both the in vitro transwell model and the in vivo skin-based experiments would allow us to optimize the amount of MIP-3α necessary for in vivo immunization studies.

If Langerhans' cell isolation poses a significant challenge, we will use splenic dendritic cell's, freshly isolated from spleens of BALB/C mice. plenic dendritic cell's will be isolated from freshly harvested spleens of BALB/C mice (6-9 weeks old, female, Jackson Labs, ME). Briefly, cell suspensions will be prepared by mechanically dissociating the spleen (in 1% FBS/HBSS) using forceps, followed by collagenase treatment (1% collagenase, NJ for 1 hour 37° C.) and erythrocyte lysis (3 minutes in 3 mL of ACK lysis buffer, BioWhittaker, MD). A Dynabead™ (Dynal Biotech) magnetic separation process using a monocolonal antibody against CD11c (Ebiosciences Inc, CA) will be used to positively select dendritic cells according to standard protocols (Dynal Biotech).

In vivo immunization using surface-modified polymer particles with or without sustained release of MIP-3α and evaluate adjuvant effects of the polymer formulations.

Preliminary studies on in vivo immunization with formulations developed as described above will be carried out in order to evaluate the adjuvant effects of the proposed polymeric delivery systems and to correlate immune response with the dendritic cell activation and Langerhans' cell migration data. We will use a plasmid encoding for the hepatitis B surface antigen (pgWiz-HBsAg, Aldevron LLC, ND) as model DNA vaccine. The following variables are proposed in the formulation design and needs to be evaluated along with appropriate controls: (a) branched versus linear PEI, (b) molecular weights of branched PEI, (c) pDNA dose, (d) co-delivery of CpG oligonucleotides with pDNA in the same particles, (e) co-delivery of MIP-3α in degradable networks, and (e) MIP-3α dose. The following criteria will be used to determine which formulations will be tested for animal studies: (i) In-vitro transfection of RAW cells and BMDC's will be used to select for the optimal molecular weight of branched PEI, (ii) The Transwell and quantitative microscopy assays described above will be used to identify optimal dose of MIP-3α. The top two doses of MIP-3α producing most potent dendritic cell attraction will be used for further in vivo analysis.

We propose to use three sets of preliminary experiments to identify effective formulations. The following tables summarize the experimental design for these studies. All groups will be given one booster application at 3 weeks after the first immunization using the same dose of pDNA. Each set of experiments will be repeated twice to ensure reproducibility. Study 1, Comparison between branched and linear PEI and optimization of pDNA dose is shown in Table 3.

TABLE 3

| | Description | pDNA dose/mouse | Number of mice |
|---|---|---|---|
| Group 1 | Saline Control | 0 | 5 |
| Group 2 | Recombinant HBsAg with Alum | 0 (0.8 ug/mice protein dose, subcutaneous) | 5 |

TABLE 3-continued

|  | Description | pDNA dose/mouse | Number of mice |
|---|---|---|---|
| Group 3 | Naked pDNA | 1, 10 or 50 ug | 5 per dose |
| Group 4 | PLGA-bPEI-pHBsAg | 1, 10 or 50 ug | 5 per dose |
| Group 5 | PLGA-lPEI-pHBsAg | 1, 10 or 50 ug | 5 per dose |

At the completion of Study 1 (with two repeats) we would choose the PEI formulation and pDNA dose generating the highest immune response. This formulation will be used for Study 2: Can CpG co-loading enhance immune response? (Table 4).

TABLE 4

|  | Description | pDNA dose/mouse | Number of mice |
|---|---|---|---|
| Group 1 | Saline Control | 0 | 5 |
| Group 2 | Recombinant HBsAg with Alum | 0 (0.8 ug/mice protein dose, subcutaneous) | 5 |
| Group 3 | Naked pDNA | Optimized dose from Exp1 | 5 |
| Group 4 | PLGA-optimizedPEI-pHBsAg | Optimized dose from Exp1 | 5 |
| Group 5 | PLGA-optimizedPEI-pHBsAg + co-loaded CpG | Optimized dose from Exp1 | 5 |

At the conclusion of Study 2, we would decide if CpG oligonucleotides, co-loaded on the same polymer particles provides any additional immunological benefit. If no significant difference is observed, subsequent studies will use pDNA alone. Study 3, shown in Table 5 will ask: Can sustained release of delivery of MIP-3α enhance immune response?

TABLE 5

|  | Description | pDNA dose/mouse | Number of mice |
|---|---|---|---|
| Group 1 | Saline Control | 0 | 5 |
| Group 2 | Recombinant HBsAg with Alum | 0 (0.8 ug/mice protein dose, subcutaneous) | 5 |
| Group 3 | Naked pDNA | Optimized dose from Exp1 | 5 |
| Group 4 | PLGA-optimizedPEI-pHBsAg-optimized CpG (from Exp 2) | Optimized dose from Exp1 | 5 |
| Group 5 | PLGA-optimizedPEI-pHBsAg-optimized CpG (from Exp 2) + MIP-3 in hydrogel dose 1 | Group 5 | 5 |
| Group 6 | PLGA-optimizedPEI-pHBsAg-optimized CpG (from Exp 2) + MIP-3 in hydrogel dose 2 | Optimized dose from Exp1 | 5 |
| Group 7 | PLGA-optimizedPEI-pHBsAg-optimized CpG (from Exp 2) + bolus MIP-3 dose 1 | Optimized dose from Exp1 | 5 |
| Group 8 | PLGA-optimizedPEI-pHBsAg-optimized CpG (from Exp 2) + bolus MIP-3 dose 2 | Optimized dose from Exp1 | 5 |

At the end of these experiments the top two formulations showing the highest immunological response will be further evaluated using 15 mice per group to establish reproducibility and variability.

Immunological assays performed for each immunization experiment: At 3, 6, and 9 weeks after initial immunization, blood (~60 µl/mouse) will be collected via retro-orbital bleeding. Serum levels of anti-HBsAg antibodies (total IgG, IgG2a, IgG1 and IgG3) will be measured by ELISA using anti-mouse secondary antibodies (Southern Biotech Inc.) Briefly, 50 µl of a 2 µg/mL solution of recombinant HBSAg (Aldevron, N. Dak.) in PBS would be incubated overnight in high binding ELISA plates. (Costar, Fisher Scientific). Plates would be washed 2× with PBST (containing 0.05% Tween 20) and blocked subsequently with PBS containing 1% BSA for 2 hours at room temperature and washed. Control mouse serum, serial dilutions of recombinant HBSAg specific monoclonal antibody (Clone NF5 (Aldevron, N. Dak.) for standard curve) and serial dilutions of serum samples from immunized mice would be incubated for 1.5 hour at room temperature. HRP conjugated rabbit anti mouse IgG would be used as the secondary antibody and developed using TMB.

Following the 9-week bleeding, mice will be euthanized and the spleen and lymph will be collected and assayed for antigen specific responses. This will include MHC Class II restricted T cell proliferation response and MHC Class I restricted ELISPOT assays for cytokine release assays (mouse IFN-gamma ELISPOT, BD Biosciences, Cat #551083). Spleen and lymph nodes from each group would be pooled together, crushed with the rear end of a 5 cc syringe plunger and passed through a 70 µm cell strainer (BD Biosciences, Cat #352350) to obtain single cell suspensions. Spleen suspensions would be seeded at varying cell numbers and pulsed with recombinant HBsAg protein (Clone NF5 (Aldevron, LLC, ND), with ovalbumin as negative control and Concanavalin A as positive control (Sigma Aldrich, MO), incubated for 20 hours with $^3$H thymidine and would be counted with a beta plate reader following cell harvesting. For MHC class I restricted CD8$^+$ T cell response spleen suspensions prepared as before would be pulsed with MHC class I restricted peptides and control peptides for HBsAg, IPQSLD-SWWTSL, the H-2L$^d$ epitope corresponding to residues 28-39 of HBsAg (Multiple Peptide Systems, CA), a 9mer H-2L$^d$ restricted epitope encoding for the 876-884 amino acid residues from the β-galactosidase protein would be used as the negative control and Concanavalin A would be used as the positive control. Following 24 hours of incubation, gamma-interferon ELISPOT assay will be performed according to manufacturer's protocol (BD Biosciences, CA). All formulations will be evaluated for strength, duration, and nature of immune response.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents inform and function, as will occur to those ordinarily skilled in the pertinent art and having the benefit of this disclosure. The depicted and described embodiments of this disclosure are examples only, and are not exhaustive of the scope of the disclosure.

What is claimed is:

1. A particle composition comprising:
   a poly(lactide-coglycolide) (PLGA) microparticle or nanoparticle comprising:
   a plurality of PLGA polymers covalently surface functionalized by a plurality of polyethyleneimine (PEI) moieties in a graft copolymer.

2. The particle composition of claim 1, further comprising at least one agent chosen from a therapeutic agent, a diagnostic agent, an imaging agent, a nucleic acid, a pDNA, an immunomodulatory agent, a cytokine, a chemokine, a chemo-attractant, an siRNA, a CpG oligonucleotide, a protein, and a peptide.

3. The particle composition of claim 1, further comprising a biodegradable polymer network, in which the microparticle or nanoparticle may be entrapped.

4. The particle composition of claim 1, wherein the plurality of PEI moieties is capable of enhancing the transfection of the particle composition.

5. The particle composition of claim 1, further comprising at least one targeting ligand.

6. The particle composition of claim 1, further comprising at least one targeting ligand chosen from a sugar, a mannose, a fructose, a galactose, a protein, a monoclonal antibody, and a fragment thereof.

7. A combinatorial delivery polymer comprising:
   a poly(lactide-coglycolide) (PLGA) microparticle or nanoparticle comprising a plurality of PLGA polymers covalently surface functionalized by a plurality of polyethyleneimine (PEI) moieties in a graft copolymer; and
   a plurality of nucleic acids electrostatically bonded to the PEI moieties in the particles.

8. The combinatorial delivery polymer of claim 7, wherein the nucleic acids comprise at least one molecule chosen from an siRNA, a pDNA and a CpG oligonucleotide.

9. The combinatorial delivery polymer of claim 7, wherein the microparticle or nanoparticle further comprises at least one agent chosen from a therapeutic agent, a diagnostic agent, an imaging agent, an immunomodulatory agent, a cytokine, a chemo-attractant, a protein, and a peptide.

10. The combinatorial delivery polymer of claim 7, wherein the microparticle or nanoparticle further comprises at least one targeting ligand.

11. The combinatorial delivery polymer of claim 7, wherein the microparticle or nanoparticle further comprises at least one targeting ligand chosen from a sugar, a mannose, a fructose, a galactose, a protein, a monoclonal antibody, and a fragment thereof.

12. The combinatorial delivery polymer of claim 7, further comprising a plurality of chemokine molecules.

13. The combinatorial delivery polymer of claim 7, further comprising a biodegradable polymer network, in which the microparticle or nanoparticle and a plurality of chemokine molecules may be entrapped.

14. The combinatorial delivery polymer of claim 12, wherein the plurality of chemokine molecules comprises at least one molecule chosen from MIP-3β, MIP-3α, a monocyte chemotactic protein, MCP-1, and MCP-3.

15. The combinatorial delivery polymer of claim 13, wherein the biodegradable polymer network is an in situ crosslinking, biodegradable, hydrogel network.

16. The particle composition of claim 1, wherein the microparticle or nanoparticle has a Zeta potential of at least 1 mV at pH 7.4 in 1 mM HEPES buffer.

17. The combinatorial delivery polymer of claim 7, wherein the microparticle or nanoparticle has a Zeta potential of at least 1 mV at pH 7.4 in 1 mM HEPES buffer.

18. A particle composition comprising:
   a poly(lactide-coglycolide) (PLGA) microparticle or nanoparticle comprising:
   a plurality of PLGA polymers covalently bonded to the PEI moieties in a graft copolymer
   wherein the microparticle or nanoparticle is operable to electrostatically bind a nucleic acid via the PEI moieties.

19. The particle composition of claim 18, further comprising at least one agent chosen from a therapeutic agent, a diagnostic agent, an imaging agent, a nucleic acid, a pDNA, an immunomodulatory agent, a cytokine, a chemokine, a chemo-attractant, an siRNA, a CpG oligonucleotide, a protein, and a peptide.

20. The particle composition of claim 18, further comprising a polymer network.

21. The particle composition of claim 18, wherein the plurality of PEI moieties is capable of enhancing the transfection of the particle composition.

22. The particle composition of claim 18, further comprising at least one targeting ligand.

23. The particle composition of claim 18, further comprising at least one targeting ligand chosen from a sugar, a mannose, a fructose, a galactose, a protein, a monoclonal antibody, and a fragment thereof.

24. The particle composition of claim 18, further comprising a particulate carrier system or a drug particle.

25. The particle composition of claim 18, wherein the microparticle or nanoparticle has a Zeta potential of at least 1 mV at pH 7.4 in 1 mM HEPES buffer.

26. The particle composition of claim 1, wherein the PEI is attached to the PLGA via carbodiimide chemistry.

27. The combinatorial delivery polymer of claim 7, wherein the PEI is attached to the PLGA via carbodiimide chemistry.

28. The particle composition of claim 18, wherein the PEI is attached to the PLGA via carbodiimide chemistry.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: oligonucleotide

<400> SEQUENCE: 1
tccatgacgt tcctgacgtt                                            20